(12) United States Patent
Bell et al.

(10) Patent No.: US 11,643,656 B2
(45) Date of Patent: May 9, 2023

(54) ANTISENSE THERAPIES FOR TREATING CANCER

(71) Applicant: The Regents of the University of California, Oakland, CA (US)

(72) Inventors: Robert J. A. Bell, Oakland, CA (US); Joseph F. Costello, Oakland, CA (US); Daniel Lim, Oakland, CA (US); Andrew Mancini, Oakland, CA (US)

(73) Assignees: THE REGENTS OF THE UNIVERSITY OF CALIFORNIA, Oakland, CA (US); THE UNITED STATES GOVERNMENT REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/615,287

(22) PCT Filed: May 24, 2018

(86) PCT No.: PCT/US2018/034313
§ 371 (c)(1),
(2) Date: Nov. 20, 2019

(87) PCT Pub. No.: WO2018/217975
PCT Pub. Date: Nov. 29, 2018

(65) Prior Publication Data
US 2020/0157536 A1 May 21, 2020

Related U.S. Application Data

(60) Provisional application No. 62/510,613, filed on May 24, 2017.

(51) Int. Cl.
| | | |
|---|---|---|
| C07H 21/04 | (2006.01) |
| C12N 15/113 | (2010.01) |
| A61K 47/68 | (2017.01) |
| A61K 9/51 | (2006.01) |
| A61K 31/7088 | (2006.01) |
| A61K 45/06 | (2006.01) |

(52) U.S. Cl.
CPC .............. *C12N 15/113* (2013.01); *A61K 9/51* (2013.01); *A61K 31/7088* (2013.01); *A61K 45/06* (2013.01); *A61K 47/6807* (2017.08); *C12N 2310/11* (2013.01); *C12N 2310/14* (2013.01); *C12N 2310/3231* (2013.01); *C12N 2310/3513* (2013.01)

(58) Field of Classification Search
None
See application file for complete search history.

(56) References Cited

U.S. PATENT DOCUMENTS

| | | |
|---|---|---|
| 2007/0203083 A1 | 8/2007 | Mootha et al. |
| 2008/0318228 A1 | 12/2008 | Lee et al. |
| 2009/0215178 A1 | 8/2009 | Tang |
| 2015/0191724 A1 | 7/2015 | Dreyfuss et al. |

FOREIGN PATENT DOCUMENTS

| | | |
|---|---|---|
| CN | 102753164 A | 10/2012 |
| EP | 2866822 A1 | 5/2015 |
| WO | 0147944 A2 | 7/2001 |
| WO | 2012177639 A2 | 12/2012 |
| WO | 2016183402 A2 | 11/2016 |

OTHER PUBLICATIONS

Vinagre et al. ("Frequency of TERT promoter mutations in human cancers." Nature communications 4.1 (2013): 1-6) describes numerous types of cancers with mutations in the TERT promoter (see Table 1).*
Stern et al. ("Mutation of the TERT promoter, switch to active chromatin, and monoallelic TERT expression in multiple cancers." Genes & development 29.21 (2015): 2219-2224) describes a correlation between the TERT promoter mutation in numerous cancers and the upregulation of GABPB1 (see abstract and p. 2219).*
International Search Report and the Written Opinion from PCT/US2018/034313 dated Sep. 25, 2018, 13 pages.
Robert J.A. Bell, et al., "The Transcription Factor GABP Selectively binds and Activates the Mutant TERT Promoter in Cancer," Science, May 29, 2015, 348(6238): 1036-1039; Abstract. doi:10.1126/science.aab0015.
Akincilar et al., "Long-Range Chromatin Interactions Drive Mutant TERT Promoter Activation," Cancer Discovery, vol. 6, No. 11, Nov. 1, 2016, pp. 1276-1292.
Application No. CN201880034152.X, Office Action, dated Jul. 26, 2022, 12 pages.
Application No. EP18805268.2, Extended European Search Report, dated Feb. 15, 2021, 13 pages.
GB1917641.1, First Examination Report, dated Oct. 11, 2021, 2 pages.
Application No. IL270820, Office Action, dated Sep. 13, 2022, 4 pages.
Mancini et al., "Disruption of the [beta]1L Isoform of GABP Reverses Glioblastoma Replicative Immortality in a TERT Promoter Mutation-Dependent Manner," Cancer Cell, vol. 34, No. 3, Sep. 1, 2018, pp. 513-528.
Application No. PCT/US2018/034313, International Preliminary Report on Patentability, dated Dec. 5, 2019, 9 pages.

(Continued)

*Primary Examiner* — Kimberly Chong
(74) *Attorney, Agent, or Firm* — Kilpatrick Townsend & Stockton LLP

(57) ABSTRACT

The present invention provides methods for cancers associated with a TERT promoter mutation in a subject. In some embodiments, the methods comprise administering to the subject a therapeutically effective amount of an agent that specifically reduces or inhibits GA binding protein transcription factor beta subunit 1 long isoform (GABPB1L) expression or function.

12 Claims, 14 Drawing Sheets

Specification includes a Sequence Listing.

(56) References Cited

OTHER PUBLICATIONS

Rahme et al., "GABP [beta] 1L Wakes Up TERT," Cancer Cell, vol. 34, No. 3, Sep. 10, 2018, pp. 358-360.
Makowski et al., "An interaction proteomics survey of transcription factor binding at recurrent TERT promoter mutations," Proteomics 2016, No. 16, pp. 417-426.

* cited by examiner

ANTISENSE THERAPIES FOR TREATING CANCER

CROSS-REFERENCE TO RELATED APPLICATIONS

This application is a 35 U.S.C. 371 U.S. National Phase application from PCT/US2018/034313, filed May 24, 2018, which claims the benefit of U.S. Provisional Application No. 62/510,613 filed on May 24, 2017, the contents of which are hereby incorporated by reference in their entireties for all purposes.

The Sequence Listing written in file 70840835_1_sequence_listing_1163030.txt created on Oct. 23, 2019, 7,265 bytes, machine format IBM-PC, MS-Windows operating system, in accordance with 37 C.F.R. 1.821- to 1.825, is hereby incorporated by reference in its entirety for all purposes.

BACKGROUND OF THE INVENTION

A telomere is a repeating DNA sequence found at each of the two ends of the body's chromosomes that allow the ends of chromosomes to be replicated. Telomerase is an enzyme that adds multiple copies of the same telomere DNA sequences to the ends of the chromosomes. Telomerase is expressed in fetal tissues, adult germ cells, and tumor cells. Because somatic (body) cells do not regularly express telomerase, these cells age or senesce due to the shortening of chromosomal telomeres. In cancer cells, telomerase is often reactivated resulting in replicative immortality. If telomerase activity is reduced in cancer cells, then the telomeres in these cells would shorten, which would prevent cancer cells from dividing.

Telomerase reverse transcriptase (TERT) is a catalytic subunit of telomerase. TERT catalyzes the addition of nucleotides in a specific DNA sequence to the ends of a chromosome's telomeres. This addition of repetitive DNA sequences prevents degradation of the chromosomal ends after multiple rounds of replication. Reactivation of telomerase reverse transcriptase (TERT) expression occurs in many human cancers. TERT reactivation is necessary to overcome replicative senescence (aging) and prevent apoptosis (cell death), both fundamental steps in the initiation of cancer. Therefore, compositions and methods for treating cancers associated with a TERT promoter mutation are needed.

BRIEF SUMMARY OF THE INVENTION

The present invention is directed to methods and compositions for treating cancers associated with a TERT promoter mutation(s). The inventors have discovered that the long isoform of GA binding protein transcription factor beta subunit 1 (GABPB1L) is necessary to activate a mutant TERT promoter. Furthermore, the inventors have discovered that specific inhibitors of GABPB1L, for example, antisense oligonucleotides (ASO) that specifically target exon 9 or the 3' untranslated region (UTR) of GABPB1L mRNA, can be used to reduce TERT expression and thus treat cancers harboring TERT promoter mutations.

In some embodiments, the present invention provides a method for treating a cancer associated with a TERT promoter mutation in a subject comprising administering to the subject a therapeutically effective amount of an agent that specifically reduces or inhibits GA binding protein transcription factor beta subunit 1 long isoform (GABPB1L) expression or function, thereby treating a cancer associated with a TERT promoter mutation.

In some examples, the method further comprises identifying one or more mutations in the TERT promoter of the subject prior to administering an agent that specifically inhibits or reduces GABPB1L expression or function. In some examples, the agent is an antisense oligonucleotide comprising a sequence that specifically hybridizes to a nucleic acid sequence in the 3' UTR of a GABPB1L mRNA. In some examples, the antisense oligonucleotide comprising a sequence that specifically hybridizes to a nucleic sequence in the 3' untranslated region (UTR) of a GABPB1L mRNA is an antisense oligonucleotide comprising a nucleotide sequence that is complementary to the sequence set forth as SEQ ID NO: 1, SEQ ID NO: 2 or SEQ ID NO: 3. In some embodiments, the antisense oligonucleotide that is complementary to the sequences set forth in SEQ ID NO: 1-3 incorporates one or more nucleic acid analogues. In some embodiments, the nucleic acid analogue is a Locked Nucleic Acid. In some examples, the agent is an antisense oligonucleotide comprising a sequence that specifically hybridizes to a nucleic acid sequence of a GABPB1L mRNA, wherein the nucleic acid sequence encodes exon 9 of GABPB1L. In some examples, the antisense oligonucleotide comprising a sequence that specifically hybridizes to a nucleic acid sequence of a GABPB1L mRNA, wherein the nucleotide sequence encodes exon 9 of GABPB1L, is an antisense oligonucleotide comprising a nucleotide sequence that is complementary to the sequence set forth as SEQ ID NO: 4, SEQ ID NO: 5 or SEQ ID NO: 6. In some embodiments, the antisense oligonucleotide that is complementary to the sequences set forth in SEQ ID NOs: 4-6 incorporates one or more nucleic acid analogues. In some embodiments, the nucleic acid analogue is a Locked Nucleic Acid. In some embodiments, the antisense oligonucleotide sequence has one or more nucleic acid analogues.

In some examples, the nucleic acid analog(s) in the antisense oligonucleotide is a locked nucleic acid (LNA). In some example, the antisense oligonucleotide is between about 10 and about 50 nucleotides in length. In some example, the antisense oligonucleotide is between about 13 and about 25 nucleotides in length.

In some examples, the cancer is selected from the group consisting of skin cancer, head and neck cancer, glioblastoma, ovarian cancer, bladder cancer, thyroid cancer, renal cancer, bladder cancer, and liver cancer.

In some examples, the method further comprises administering another cancer therapy to the subject. In some examples, the cancer therapy is selected from the group consisting of radiation therapy, chemotherapy and surgery.

In some embodiments, the present invention provides antisense oligonucleotide of between about 10 and about 50 nucleotides in length, wherein the antisense oligonucleotide comprises a sequence that is complementary to the sequence set forth in any one of SEQ ID NOs: 1, 2, 3, 4, 5 or 6. In some examples the antisense oligonucleotide is between about 13 and about 25 nucleotides in length.

BRIEF DESCRIPTION OF THE DRAWINGS

The present application includes the following figures. The figures are intended to illustrate certain embodiments and/or features of the compositions and methods, and to supplement any description(s) of the compositions and methods. The figures do not limit the scope of the compositions and methods, unless the written description expressly indicates that such is the case.

FIG. 5(*a*) shows the three LNA-ASOs targeted against exon 9 of GABPB1L. FIG. 5(*b*) shows the three LNA-ASOs targeted against the UTR region of GABP1L.

DEFINITIONS

Figures 1A, 1B, 1C:
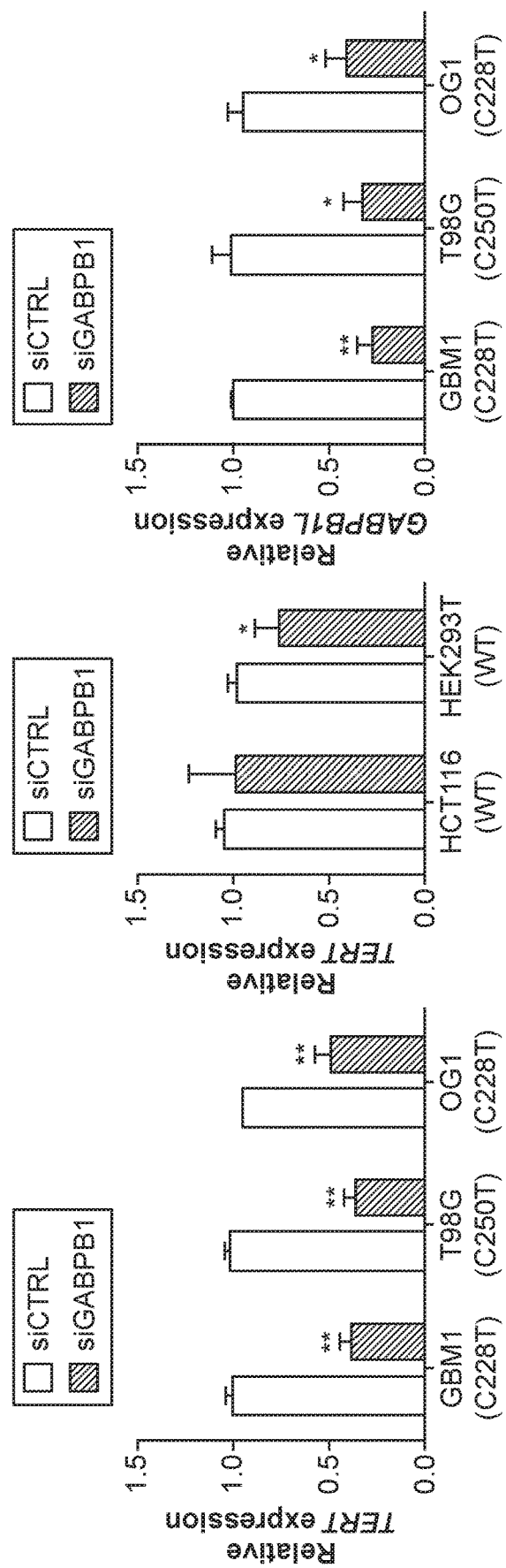
FIG. 1 shows that GABPB1L was required for activation of the mutant TERT promoter. (a, b) TERT expression following siRNA-mediated knockdown of GABPB1 in (a) TERT promoter mutant or (b) TERT promoter-wild-type lines. GBM1 and T98G are TERT promoter mutant primary GBM lines, and OG1 is a patient-derived TERT promoter mutant recurrent oligodendroglioma line. *P<0.05, **P<0.01, two-sided Student's t-test compared to siControl (siCTRL) in each respective line. Values are mean±S.D. of at least three independent experiments (two independent experiments for OG1 and HCT116 lines). (c) GABPB1L expression following siRNA-mediated knockdown of GABPB1 in TERT promoter mutant lines from (a). *P<0.05, **P<0.01, two-sided Student's t-test compared to siControl (siCTRL) in each respective line. Values are mean±S.D. of at least three independent experiments (two independent experiments or OG1 line).

As used in this specification and the appended claims, the singular forms "a," "an," and "the" include plural reference unless the context clearly dictates otherwise.

The term "nucleic acid" refers to deoxyribonucleic acids (DNA) or ribonucleic acids (RNA) and polymers thereof in either single- or double-stranded form. Unless specifically limited, the term encompasses nucleic acids containing known analogues of natural nucleotides, including but not limited to Locked Nucleic Acids (LNAs), Bridged Nucleic acids (BNAs), peptide nucleic acids (PNAs), ethylene-bridged nucleic acids (ENAs), 2'-O-methyl (2-OMe) modified RNA, 2'-O-methoxyethyl (2-MOE) modified RNA, hexitol nucleic acids, and nucleotides with phosphorothioated backbones that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene. Thymine (T) and uracil (U) are used interchangeably in nucleic acids according to the type of polynucleotide (DNA or RNA).

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods of the present invention includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side-effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition. The term "treatment," as used herein, includes preventative (e.g., prophylactic), curative or palliative treatment.

A "promoter" is defined as one or more a nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

"Polypeptide," "peptide," and "protein" are used interchangeably herein to refer to a polymer of amino acid residues. As used herein, the terms encompass amino acid chains of any length, including full-length proteins, wherein the amino acid residues are linked by covalent peptide bonds.

As used herein, an "antisense oligonucleotide" is a nucleic acid sequence (DNA, RNA, or a nucleotide analogue) that is complementary to messenger RNAs (mRNAs), hybridizes to and inactivates the mRNA sequence, e.g., makes the mRNA sequence unavailable for translation or targets the mRNA for destruction. In some embodiments, the antisense oligonucleotide that specifically binds to or hybridizes to a noncoding or a coding region of a mRNA encoding GABPB1L. Antisense oligonucleotides that specifically bind or hybridize to a mRNA encoding GABPB1L do not hybridize or bind to an mRNA encoding the short isoform of GABPB1 (GABPB1S) or a mRNA encoding GA binding protein transcription factor beta subunit 2 (GABPB2). In some examples, the antisense oligonucleotide is between about 10 and about 50 nucleotides in length. For example, the antisense oligonucleotide can be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length. In some examples, the antisense oligonucleotide can be between about 10 and about 40 nucleotides in length, between about 10 and 30 nucleotides in length, between about 10 and 25 nucleotides in length, between about 12 and about 50 nucleotides in length, between about 12 and about 40 nucleotides in length, between about 12 and about 30 nucleotides in length, between about 12 and 25 nucleotides in length, between about 13 and about 40 nucleotides in length, between about 13 and about 30 nucleotides in length, or between about 13 and about 25 nucleotides in length.

The antisense oligonucleotides provided herein decrease TERT expression in TERT promoter mutant cells, thus decreasing telomerase activity in a TERT promoter mutant cell. This decrease in expression can be about 10%, 20%, 30%, 40%, 50%, 60%, 70%, 80%, 90%, 100% or any percentage in between as compared to a control cell or a control value. Generally, the antisense oligonucleotide sequence that specifically hybridizes to a noncoding or a coding region of a mRNA encoding GABPB1L is designed to complement (e.g., perfectly complement) or substantially complement (e.g., having 1-4 mismatches) a nucleic acid sequence in a GABPB1L mRNA, for example, a nucleic acid sequence in the 3'UTR or a nucleic acid sequence encoding exon 9 of a GABPB1L mRNA, for example, a human GABPB1L mRNA. In some cases, the antisense oligonucleotide can be altered or designed using routine methods to avoid or reduce secondary structure formation. In some cases, the antisense oligonucleotide can be designed to optimize G-C content. In some cases, G-C content is preferably between about 40% and about 60% (e.g., 40%, 45%, 50%, 55%, 60%).

As used herein, the term "complementary" or "complementarity" refers to specific base pairing between nucleotides or nucleic acids. In some embodiments, for example, and not to be limiting, base pairing between an antisense oligonucleotide and a target nucleic acid sequence in a GABPB1L mRNA is described. Complementary nucleotides are, generally, adenine (A) and thymine (T) (or A and uracil (U)), and guanine (G) and cytosine (C). As set forth above, the antisense oligonucleotides described herein can be perfectly complementary or substantially complementary (e.g., having 1-4 mismatches) to a nucleic acid sequence in a GABPB1L mRNA.

As used throughout, by subject is meant an individual. For example, the subject is a mammal, such as a primate, and, more specifically, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical uses and formulations are contemplated herein. The term does not denote a particular age or sex. Thus, adult and newborn subjects, whether male or female, are intended to be covered. As used herein, patient or subject may be used interchangeably and can refer to a subject afflicted with a disease or disorder.

As used herein, a cancer associated with one or more TERT promoter mutations can be, but is not limited to, skin cancer (e.g., base cell carcinoma, squamous cell carcinoma, Merkel cell carcinoma, pleomorphic dermal sarcoma, atypical fibroxanthoma and melanoma), head and neck cancer (e.g., laryngeal carcinoma and squamous cell carcinoma of head and neck), soft tissue and pleuron tumor (e.g., myxoid liposarcoma, solitary fibrous tumor, chondrosarcoma, fibrosarcoma, and malignant pleural mesothelioma), brain cancer (e.g., glioblastoma, oligodendroglioma, gliosarcoma, meningioma or medullobastoma), gynecological cancer (e.g., ovarian carcinoma, endometrial carcinoma and squamous cell carcinoma of the cervix), urological cancer (e.g, renal cell carcinoma, bladder cancer, ureter carcinoma, renal pelvic carcinoma, endocrine cancer (e.g. thyroid cancer and adrenocortical carcinoma), lung cancer, digestive system cancer (e.g., hepatocellular carcinoma and gastric cancer), medullary carcinoma, paragaglioma, pheochromocytoma. Phyllodes tumor and mantle cell lymphoma.

Optionally, the methods provided herein can further comprise administering another cancer therap(y/ies) to the subject such as, for example, chemotherapy, immunotherapy, radiation and/or surgery.

As used throughout, chemotherapeutic agents are compounds which can inhibit the growth of cancer cells or tumors. It is understood that one or more chemotherapeutic agents can be used in any of the methods set forth herein. For example, two or more chemotherapeutic agents, three or more chemotherapeutic agents, four or more chemotherapeutic agents, etc. can be used in the methods provided herein. Chemotherapeutic agents include adriamycin, dactinomycin, bleomycin, vinblastine, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, daunorubicin hydrochloride, decitabine, dexormaplatin, dezaguanine, dezaguanine mesylate, diaziquone, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, etoposide, etoposide phosphate, etoprine, fadrozole hydrochloride, fazarabine, fenretinide, floxuridine, fludarabine phosphate, fluorouracil, flurocitabine, fosquidone, fostriecin sodium, gemcitabine, gemcitabine hydrochloride, hydroxyurea, idarubicin hydrochloride, ifosfamide, ilmofosine, interleukin II (including recombinant interleukin II, or rIL2), interferon alfa-2a, interferon alfa-2b, interferon alfa-nl, interferon alfa-n3, interferon beta-1a, interferon gamma-1 b, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safingol, safingol hydrochloride, semustine, simtrazene, sparfosate sodium, sparsomycin, spirogermanium hydrochloride, spiromustine, spiroplatin, streptonigrin, streptozocin, sulofenur, talisomycin, tecogalan sodium, tegafur, teloxantrone hydrochloride, temoporfin, teniposide, teroxirone, testolactone, thiamiprine, thioguanine, thiotepa, tiazofurin, tirapazamine, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

As used herein, "safe and effective amount" refers to the quantity of an agent that is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of an agent effective to yield the desired therapeutic response, for example, an amount effective to delay the growth of a cancer or to cause a cancer to decrease in size or not metastasize. The specific safe and effective amount or therapeutically effective amount will vary with such factors as the particular condition being treated, the physical condition of the patient, the type of subject being treated, the duration of the treatment, the nature of concurrent therapy (if any), and the specific formulations employed and the structure of the compounds or its derivatives.

DETAILED DESCRIPTION OF THE INVENTION

The following description recites various aspects and embodiments of the present compositions and methods. No particular embodiment is intended to define the scope of the compositions and methods. Rather, the embodiments merely provide non-limiting examples of various compositions and methods that are at least included within the scope of the disclosed compositions and methods. The description is to be read from the perspective of one of ordinary skill in the art, therefore, information well known to the skilled artisan is not necessarily included.

Mutations, including non-coding mutations, in the TERT promoter region of many cancer cells have been found. Although not bound by any mechanism, the high prevalence of TERT promoter mutations in various cancers and their direct correlation with increased TERT transcription, telomere length and telomerase activity in primary tumors suggest that TERT promoter mutations represent a fundamental mechanism of telomerase reactivation in human cancers.

Provided herein are compositions and methods for treating cancers associated with one or more TERT promoter mutations. The inventors have surprisingly discovered that GABPB1L is necessary to activate a mutant TERT promoter. Furthermore, the inventors have discovered that specific inhibitors or reducers of GABPB1L expression or function, for example, antisense oligonucleotides (ASO) that specifically target exon 9 or the 3' untranslated region (UTR) of GABPB1L mRNA, can be used to reduce TERT expression and thus treat cancers harboring TERT promoter mutations. By specifically targeting and reducing GABPB1L expression or function, TERT expression is decreased, thus reducing TERT reactivation in cancers associated with one or more TERT promoter mutations.

Methods

Described herein is a method for treating a cancer associated with a TERT promoter mutation in a subject comprising administering to the subject a therapeutically effective amount of an agent that specifically reduces or inhibits GA binding protein transcription factor beta subunit 1 long isoform (GABPB1L) expression or function, thereby treating a cancer associated with a TERT promoter mutation. In some examples, the cancer is associated with one or more mutations in the TERT promoter. These include but are not limited to C228T (on chromosome 5 (hg19 genomic coordinate 1295228)), C228A (on chromosome 5 (hg19 genomic coordinate 1295228)), C250T (on chromosome 5 (hg19 genomic coordinate 1295250)), A161C (hg19 genomic coordinate 1295161), a tandem mutation comprising a C228T mutation (on chromosome 5 (hg19 genomic coordinate 1295228)) and a C229T mutation (on chromosome 5 (hg19 genomic coordinate 1295229)), and a tandem mutation comprising a C242T mutation (on chromosome 5 (hg19 genomic coordinate 1295242)) and a C243T mutation (on chromosome 5 (hg19 genomic coordinate 1295243)). Optionally, the method further comprises identifying one or more mutations in the TERT promoter of the subject prior to administering a therapeutically effective amount of an agent that specifically inhibits or reduces GABPB1L expression or function. Methods for identifying one or more mutations in the TERT promoter are known to those of skill in the art. These include, for example, techniques such as nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization and electrophoretic mobility shift assay (EMSA).

In some examples, the agent that specifically inhibits or reduces GABPB1L function is an antisense oligonucleotide, an siRNA, a morpholino, a locked nucleic acid (LNA), an miRNA, a bridged nucleic acid (BNA), a peptide nucleic acid (PNA), an ethylene-bridged nucleic acid (ENA), a 2'-O-methyl (2-OMe) modified RNA, a 2'-O-methoxyethyl (2-MOE) modified RNA, a hexitol nucleic acid, and/or an oligonucleotide with a phosphorothioated backbone. In some examples, one or more agents that specifically inhibit GABPB1L are administered. In some examples, the one or more agents specifically inhibits or reduces GABPB1L expression or function are administered.

In some examples, the antisense oligonucleotide, LNA or siRNA comprises a sequence that specifically hybridizes to a nucleic acid sequence in the 3' UTR of a GABPB1L mRNA. An example of a GABPB1L nucleotide sequence that can be targeted using the methods and compositions provided herein is set forth as SEQ ID NO: 13. This sequence comprises exon 9 and the 3'UTR of GABPB1L. The sequence of the 3' UTR of GABPB1L is provided herein as SEQ ID NO: 14. Antisense oligonucleotides that specifically hybridize to or are complementary to a nucleic acid sequence in SEQ ID NO: 14 can be designed using routine methods. For example, antisense oligonucleotides of about 14 nucleotides in length to about 25 nucleotides in length that specifically hybridize to or are complementary to a nucleic acid sequence in SEQ ID NO: 14 can be designed based on SEQ ID NO: 14. In some examples, the antisense oligonucleotide specifically hybridizes to or is complementary to a nucleic acid sequence in the 3' UTR of a GABPB1L mRNA comprising SEQ ID NO: 1 (GATCGTTGTTGGT-TAG), SEQ ID NO: 2 (ACTGGCAGACTGTTCA) or SEQ ID NO: 3 (TAATTATGGTGGACTG). In some embodiments, one or more of the nucleotides in SEQ ID NOs: 1-3 is a nucleic acid analogue. In some embodiments, one or more of the nucleotides in SEQ ID NOs:1-3 is a Locked Nucleic Acid. Examples of antisense oligonucleotides that specifically hybridize to or are complementary to a nucleic acid sequence in the 3' UTR of a GABPB1L mRNA include, but are not limited to SEQ ID NO: 7 (CTAACCAACAAC-GATC), SEQ ID NO: 8 (TGAACAGTCTGCCAGT) and SEQ ID NO: 9 (CAGTCCACCATAATTA). In some embodiments, one or more of the nucleotides in SEQ ID NOs: 7-9 is a nucleic acid analogue. In some embodiments, one or more of the nucleotides in SEQ ID NOs:7-9 is a Locked Nucleic Acid.

In other examples, the antisense oligonucleotide, LNA or siRNA comprises a sequence that specifically hybridizes to or is complementary to a nucleic acid sequence of a GABPB1L mRNA, wherein the nucleotide sequence encodes exon 9 of GABPB1L. The sequence of exon 9 of GABPB1L is provided herein as SEQ ID NO: 15. Antisense oligonucleotides that specifically hybridize to or are complementary to a nucleic acid sequence in SEQ ID NO: 15 can be designed using routine methods. For example, antisense oligonucleotides of about 13 nucleotides in length to about 25 nucleotides in length that specifically hybridize to or are complementary to a nucleic acid sequence in SEQ ID NO: 15 can be designed based on SEQ ID NO: 15. In some examples, the antisense oligonucleotide specifically hybridizes to or is complementary to a nucleic acid sequence comprising SEQ ID NO: 4 (TCGACAGCAGCTCCTA), SEQ ID NO: 5 (CCTACAGACAGAAGTT) or SEQ ID NO: 6 (TAAAGAAGCTGTTTAA). Examples of antisense oligonucleotides that specifically hybridize to or are complementary to a nucleic acid sequence of a GABPB1L mRNA, wherein the nucleotide sequence encodes exon 9 of GABPB1L include, but are not limited to SEQ ID NO: 10 (TAGGAGCTGCTGTCGA), SEQ ID NO: 11 (AACTCTGTCTGTAGG) and SEQ ID NO: 12 (TTAAACAGCTTCTTTA).

In some embodiments, the antisense oligonucleotide is a splice-switching antisense oligonucleotide, for example, a splice-switching LNA, that disrupt the normal splicing of the GABPB1L transcript by blocking the RNA-RNA base pairing or protein-RNA binding interactions that occur between components of the splicing machinery and the pre-mrNA. In some example, the splice-switching antisense oligonucleotide, occludes one or more splice recognition sites on the GABPB1 pre-mRNA to prevent maturation of the GABPB1L mRNA without eliciting a strong RNase H response. To prevent RNase H activation, ssLNAs alternate LNA-modified ribonucleotides and unmodified deoxyribonucleotides along the entirety of the phosphorothioate antisense oligonucleotide backbone. See, for example, Havens and Hastings "Splice-switching antisense oligonucleotides as therapeutic drugs," Nucleic Acids Res. 44(14): 6549-6563 (2016)).

One or more agents provided herein can be in a pharmaceutically acceptable carrier. The term carrier means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject. Such pharmaceutically acceptable carriers include sterile biocompatible pharmaceutical carriers, including, but not limited to, saline, buffered saline, artificial cerebral spinal fluid, dextrose, and water.

Modes of administration of the compositions used in the invention are exemplified below. Any of the GABPB1L inhibitors described herein can be delivered by any of a variety of routes including: by injection (e.g., subcutaneous, intramuscular, intravenous, intra-arterial, intraperitoneal), by continuous intravenous infusion, cutaneously, dermally, transdermally, orally (e.g., tablet, pill, liquid medicine, edible film strip), by implanted osmotic pumps, by suppository, or by aerosol spray. Routes of administration include, but are not limited to, topical, intradermal, intrathecal, intralesional, intratumoral, intrabladder, intravaginal, intraocular, intrarectal, intrapulmonary, intracranial, intraventricular, intracerebroventricular, intraspinal, dermal, subdermal, intra-articular, placement within cavities of the body, nasal inhalation, pulmonary inhalation, impression into skin, and electroporation.

In an example in which a nucleic acid is employed, such as, an antisense, a morpholino, an siRNA molecule, or a locked nucleic acid, the nucleic acid can be delivered intracellularly (for example by expression from a nucleic acid vector or by receptor-mediated mechanisms), or by an appropriate nucleic acid expression vector which is administered so that it becomes intracellular, for example by use of a retroviral vector (see U.S. Pat. No. 4,980,286), or by direct injection, or by use of microparticle bombardment (such as a gene gun; Biolistic, Dupont), or coating with lipids or cell-surface receptors or transfecting agents, or by administering it in linkage to a homeobox-like peptide which is known to enter the nucleus (for example Joliot et al., Proc. Natl. Acad. Sci. USA 1991, 88:1864-8). Nucleic acid carriers also include, polyethylene glycol (PEG), PEG-liposomes, branched carriers composed of histidine and lysine (HK polymers), chitosan-thiamine pyrophosphate carriers, surfactants, nanochitosan carriers, and D5W solution. The present disclosure includes all forms of nucleic acid delivery, including synthetic oligos, naked DNA, naked antisense oligonucleotides, plasmid and viral delivery, integrated into the genome or not. Nucleic acids can also be delivered gymnotically. See for example, Soifer et al. "Silencing of gene expression by gymnotic delivery of antisense oligonucleotides," Methods Mol. Biol. 815: 333-46 (2012), hereby incorporated in its entirety by this reference.

As mentioned above, vector delivery can be via a viral system, such as a retroviral vector system which can package a recombinant retroviral genome (see e.g., Pastan et al., Proc. Natl. Acad. Sci. U.S.A. 85:4486, 1988; Miller et al., Mol. Cell. Biol. 6:2895, 1986). The exact method of introducing the altered nucleic acid into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), and pseudotyped retroviral vectors (Agrawal et al., Exper. Hematol. 24:738-747, 1996).

The nucleic acid can also be encapsulated in a nanoparticle or chemically conjugated to a carrier. For example, the nucleic acid can be chemically conjugated to a cell or a tissue-targeting ligand, such as an antibody or a ligand for a cell-surface receptor to target nucleic acid to specific cell types or tumor environments.

Physical transduction techniques can also be used, such as liposome delivery and receptor-mediated and other endocytosis mechanisms (see, for example, Schwartzenberger et al., Blood 87:472-478, 1996) to name a few examples. This invention can be used in conjunction with any of these or other commonly used gene transfer methods.

The effective amount of an agent, for example, a safe and effective amount or a therapeutically effective amount can depend on the nature of the disease and can be determined by standard clinical techniques. Therefore, these amounts will vary. Multiple dosages can also be administered depending on the disease, and the subject's condition. In addition, in vitro assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Depending on the intended mode of administration, a pharmaceutical composition comprising one or more agents described herein can be in the form of solid, semi-solid, or liquid dosage forms, such as, for example, tablets, suppositories, pills, capsules, powders, liquids, aerosols, or suspensions, preferably in unit dosage form suitable for single administration of a precise dosage. The compositions will include a therapeutically effective amount of the agent described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

Compositions

Compositions for reducing TERT expression in a TERT promoter mutant cell or a TERT promoter mutant cancer are provided. Described herein are antisense oligonucleotides of between about 10 and about 50 nucleotides in length, wherein the antisense oligonucleotide comprises a nucleotide sequence that is complementary to a sequence in the 3'UTR of a GABPB1L mRNA or a nucleotide sequence in an GABPB1L mRNA that encodes exon 9. In some examples, the antisense oligonucleotide comprises a nucleotide sequence that is complementary to a sequence comprising SEQ ID NO: 1, SEQ ID NO: 2 or SEQ ID NO: 3 in the 3'UTR of a GABPB1L mRNA. These include, but are not limited to an antisense oligonucleotide comprising SEQ ID NO: 7, SEQ ID NO: 8 or SEQ ID NO: 9. In other examples, the antisense oligonucleotide comprises a nucleotide sequence that is complementary to a sequence comprising SEQ ID NO: 4, SEQ ID NO: 5 or SEQ ID NO: 6 in the GABPB1L mRNA sequence encoding exon 9 of GABPB1L. These include, but are not limited to an antisense oligonucleotide comprising SEQ ID NO: 10, SEQ ID NO: 11 or SEQ ID NO: 12.

In some examples, the antisense oligonucleotide is between about 10 and about 40 nucleotides in length, between about 10 and about 30 nucleotides in length or between about 10 and about 25 nucleotides in length. In some examples, the antisense oligonucleotide is between about 13 and about 40 nucleotides in length, between about 13 and about 30 nucleotides in length or between about 13 and about 25 nucleotides in length. In other examples, the antisense oligonucleotide is between about 14 and about 40 nucleotides in length, between about 14 and about 30 nucleotides in length or between about 14 and about 25 nucleotides in length. In other examples, the antisense oligonucleotide is between about 15 and about 40 nucleotides in length, between about 15 and about 30 nucleotides in length or between about 15 and about 25 nucleotides in length.

Optionally, the antisense oligonucleotides can be in a vector, for example, a plasmid or a viral vector, as described above. Optionally, the antisense oligonucleotide can be combined with or conjugated to a carrier, for example, a cell, a cell-specific ligand or a tissue-targeting ligand (e.g., an antibody or a ligand for a cell surface receptor), polyethylene glycol (PEG), PEG-liposomes, branched carriers composed of histidine and lysine (HK polymers), chitosan-thiamine pyrophosphate carriers, surfactants, nanochitosan carriers, and D5W solution. Optionally, the carrier can be a pharmaceutically acceptable carrier. Optionally, the antisense oligonucleotide can be encapsulated in a nanoparticle. A plurality of nanoparticles comprising the antisense oligonucleotides described herein are also provided.

Optionally, the antisense oligonucleotides, nanoparticles comprising the antisense oligonucleotides or antisense oligonucleotides combined with or conjugated to a carrier are in a pharmaceutically acceptable composition.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to one or more molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

The following examples are provided by way of illustration only and not by way of limitation. Those of skill in the art will readily recognize a variety of non-critical parameters that could be changed or modified to yield essentially the same or similar results.

Reactivation of telomerase reverse transcriptase (TERT) expression is necessary to overcome replicative senescence (aging) and prevent cell apoptosis. Over fifty types of cancer acquire TERT promoter mutations. These single point mutations reactivate telomerase, allowing for indefinite maintenance of telomere length and enabling cellular immortalization (Horn et al. TERT Promoter Mutations in Familial and Sporadic Melanoma. Sci. (New York, N.Y.) (2013); Huang et al. Highly Recurrent TERT Promoter Mutations in Human Melanoma. Sci. (New York, N.Y.) (2013); Arita et al. Upregulating mutations in the TERT promoter commonly occur in adult malignant gliomas and are strongly associated with total 1p19q loss. Acta Neuropathol. 126, 267-276 (2013); Killela et al. TERT promoter mutations occur frequently in gliomas and a subset of tumors derived from cells with low rates of self-renewal. Proc. Natl. Acad. Sci. 110, 6021-6026 (2013)). The transcription factor binding site created by the point mutations specifically recruit the E26 transformation-specific (ETS) factor GA-binding protein (GABP), a multimeric transcription factor composed of the GABPα and GABPβ subunits (Bell et al. Cancer. The transcription factor GABP selectively binds and activates the mutant TERT promoter in cancer. Sci. (New York, N.Y.) 348, 1036-1039 (2015); Stern et al. Mutation of the TERT-promoter, switch to active chromatin, and monoallelic TERTexpression in multiple cancers. Genome Res. (2015)).

GABP can form two functionally independent transcription factor species, a dimer or a tetramer, depending on which of the structurally distinct GABPβ isoforms is incorporated into the complex (Bell et al.; and Stern et al.). As shown herein, the GABPB1L tetramer-forming isoform was necessary to activate the mutant TERT promoter. Also demonstrated was the feasibility of engineering an antisense oligonucleotide (ASO) targeting GABPB1L to reduce TERT expression in TERT promoter mutant cells without ablating total GABP function. Finally, as shown herein, a GABPB1L-targeted ASO candidate can reduced GABPB1L levels in vivo without the assistance of a delivery agent, showing the ability of this approach to treat cancers harboring TERT promoter mutations.

Telomeres are composed of "TTAGGG" repeats at the end of chromosomes, and telomere length plays a critical role in multiple human diseases including cancer (Moyzis et al. A highly conserved repetitive DNA sequence, (TTAGGG)n, present at the telomeres of human chromosomes. 85, 6622-6626 (1988); Blasco, Telomeres and human disease: ageing, cancer and beyond. Nat. Rev. Genet. 6, 611-622 (2005)).

Telomere length is regulated by telomerase, a reverse transcriptase complex that recognizes, binds, and elongates the telomere ends using an intrinsic RNA template (Bryan & Cech, Telomerase and the maintenance of chromosome ends. Curr. Opin. Cell Biol. 11, 318-324 (1999); Greider & Blackburn, E. H. Identification of a specific telomere terminal transferase activity in tetrahymena extracts. *Cell* 43, 405-413 (1985)). The TERT gene encodes the catalytic subunit of telomerase, and its transcriptional regulation is usually the limiting step in telomerase activity (Weinrich S. L. et al. Reconstitution of human telomerase with the template RNA component hTR and the catalytic protein subunit hTRT. Nat. Genet. 17, 498-502 (1997); Nakamura et al. Telomerase catalytic subunit homologs from fission yeast and human. Sci. (New York, N.Y.) 277, 955-959 (1997); and Meyerson et al. hEST2, the putative human telomerase catalytic subunit gene, is up-regulated in tumor cells and during immortalization. Cell 90, 785-795 (1997)).

Telomerase activity is silenced in the majority of normal tissues, causing telomeres to shorten with each successive round of cell division (Hayflick & Moorhead, The serial cultivation of human diploid cell strains. Exp. Cell Res. 25, 585-621 (1961)). Eventually, a critical telomere length is reached (Hayflick & Moorhead; Cong, et al. Human telomerase and its regulation. Microbiol. Mol. Biol. Rev. 66, 407-25-table of contents (2002); Nandakumar & Cech. Finding the end: recruitment of telomerase to telomeres.

Nat. Rev. Mol. cell Biol. 14, 69-82 (2013)) and cells either enter replicative senescence or undergo programmed cell death (Huschtscha & Holliday. Limited and unlimited growth of SV40-transformed cells from human diploid MRC-5 fibroblasts. J. Cell Sci. 63, 77-99 (1983); Wright et al. Reversible cellular senescence: implications for immortalization of normal human diploid fibroblasts. 9, 3088-3092 (1989); and Counter et al. Telomere shortening associated with chromosome instability is arrested in immortal cells which express telomerase activity. 11, 1921-1929 (1992)). The reactivation or re-expression of telomerase is considered a hallmark of tumorigenesis, as over 90%0/of human cancers express telomerase to achieve replicative immortality (Kim et al. Specific Association of Human Telomerase Activity with Immortal Cells and Cancer. Sci. (New York, N.Y.) 266, 2011-2015 (1994); Phd, P. C.-B. et al. Methylation of the TERT promoter and risk stratification of childhood brain tumours: an integrative genomic and molecular study. Lancet Oncol. 14, 534-542 (2013); and Shay, J. W. & Bacchetti, S. A survey of telomerase activity in human cancer. Eur. J. Cancer 33, 787-791 (1997)).

Two hotspot point mutations were identified in the TERT promoter in 71% of melanomas (Horn et al. and Huang et al.). These mutations are located 124 and 146 base pairs upstream of the translation start site and referred to as C228T and C250T, respectively, based on their hg19 genomic coordinates. The mutations are typically heterozygous, occur in a mutually exclusive fashion, and both create identical 11 base pair sequences (CCCGGAAGGGG). Both mutations activate TERT promoter activity and TERT gene transcription. Soon after their initial discovery, the TERT promoter mutations were found to be the most common point mutations in several tumor types including 83% of glioblastoma (Killela et al.), 71% of melanoma (Horn et al. and Huang et al.), 66% of bladder cancer, and 47% of hepatocellular carcinoma (HCC) (Killela et al; and Quaas et al. Frequency of TERT promoter mutations in primary tumors of the liver. Virchows Arch. (2014)). To date, the hotspot mutations have been identified in over 50 distinct cancer types (Bell et al. Understanding TERT Promoter Mutations: A Common Path to Immortality. Mol. Cancer Res. 14, 315-323 (2016)).

On the basis of the identical 11bp DNA sequence motif created by the TERT promoter mutations, the mechanism of promoter activation was hypothesized to involve recruitment of an ETS family TF. There are 27 ETS factors, however, and most bind a very similar DNA sequence in vitro, suggesting extensive redundancy (Wei et al. Genome-wide analysis of ETS-family DNA-binding in vitro and in vivo. EMBO J. 29, 2147-2160 (2010)). It was therefore surprising that GABPA but no other ETS factors were identified to be the TF responsible for mutant TERT activation5. GABPα is the only ETS factor to selectively regulate the mutant TERT promoter without affecting wild-type promoter activity, and its binding to the mutant TERT promoter was conserved across cell lines from multiple cancer types including GBM, melanoma, HCC, and neuroblastoma. This discloses transcription factor GABP as a therapeutic target to inhibit telomerase in cancer cells harboring TERT promoter mutations.

The GABP transcription factor is an obligate multimer consisting of the DNA-binding GABPα subunit and trans-activating GABPβ subunit. GABP can act as a heterodimer (GABPαPβ) composed of one GABPα and one GABPβ subunit or a heterotetramer (GABPα2β2) composed of two GABPα and two GABPβ subunits (Rosmarin et al. GA-binding protein transcription factor: a review of GABP as an integrator of intracellular signaling and protein-protein interactions. Blood Cells. Mol. Dis. 32, 143-154 (2004)). The GABPβ subunit is encoded by two distinct genes: the GABPB1 gene encoding GABPβ1 and the GABPB2 gene encoding GABPβ2. The GABPβ1 subunit has two distinct isoforms, a short GABPB1S isoform and a longer GABPBβ1L isoform, while the GABPβ2 subunit has a single isoform (Rosmarin et al.; and De La Brousse et al. Molecular and genetic characterization of GABP beta. Genes Dev. 8, 1853-1865 (1994)). Whereas the GABPβ1S isoform is only able to dimerize with GABPα, both GABPβ1L and GABPβ2 possess a C-terminal leucine-zipper domain (LZD) that mediates the formation of the GABP heterotetramer (Rosmarin et al. and De La Brousse et al.). Although GABPβ1L or GABPβ2 form the GABP tetramer, GABP tetramers containing the GABPβ1L isoform are functionally distinct from GABPBβ2-containing tetramers and may control separate transcriptional programs (Jing et al. GABPbeta2 is dispensible for normal lymphocyte development but moderately affects B cell responses. J. Biol. Chem. 283, 24326-24333 (2008); and Yu et al. Targeting Tetramer-Forming GABPβ Isoforms Impairs Self-Renewal of Hematopoietic and Leukemic Stem Cells. Cell Stem Cell 11, 207-219 (2012)). Furthermore, while abolishing full GABP function results in early embryonic lethality in mice, knockout of the tetramer-specific transcriptional program has minimal phenotypic consequences (Jing et al.; Yu et al.; and Xue et al. Targeting the GA binding protein beta1L isoform does not perturb lymphocyte development and function. Mol. Cell. Biol. 28, 4300-4309 (2008)). Thus, determining if the mutant TERT promoter is regulated by the GABP dimer, the GABP tetramer, or both was critical to evaluating GABP as a therapeutic target. If the GABP tetramer is necessary to activate the mutant TERT promoter, the extent to which GABPβ1L and GABPβ2 are functionally redundant also impact GABP tetramer-targeted therapy.

Methods

Cell Culture—

GBM1, T98G, and U251 cells were cultured in DMEM/Ham's F-12 1:1 media, 10% FBS, 1% Penicillin/Streptomycin. The GBM1 primary culture was previously described in Bell et al. (2015). HEK293T cells were cultured in DMEM H-21 media, supplemented with 10% FBS, 1% Non-Essential Amino Acids, 1% Glutamine and 1% Penicillin/Streptomycin. HCT116 cells were cultured in McCoy's 5A media supplemented with 10% FBS and 1% Penicillin/Streptomycin. OG1 is a TERT promoter-mutant, IDH1-mutant patient-derived recurrent high-grade oligodendroglioma culture. OG1 cells were cultured in Neurocult NS-A (stem Cell Technologies) supplemented with 2 mM L-Glutamine, 1% Penicillin/Streptomycin, B-27 w/o vitamin A (Invitrogen), N2 supplement, 20 ng/mL EGF, and 20 ng/mL bFGF, and 1% sodium pyruvate. Cells were grown on 1.6 ug/cm$^2$ laminin-coated and dissociated with StemPro Accutase (Gibco). SK-MEL-28 and SNU-423 cells were cultured in RPMI-1640, 10% FBS, 1% Penicillin/Streptomycin, ad 1% Sodium Pyruvate. All cells were maintained at 37° Celsius, 5% CO2.

siRNA/LNA-ASO Knockdown—

Non-targeting, GABPB1, and GABPB2-directed siRNA pools were obtained from Dharmacon. Non-targeting, GABPA, TERT, and GABPB1-directed (B1L-1,B1L-2,B1L-3,UTR1,UTR2,UTR3) LNA-ASOs were designed and ordered from Exiqon. 100 μL of cells were seeded at a density of 30,000 cells/mL in a 96-well plate and transfected 24 hours after with a final concentration 50 nM of siRNA/LNA-ASO and 0.1 uL of Dharmafect 1 reagent (Dharmacon). At 48 hours and 72 hours post-transfection, cells were lysed and cDNA was generated using the POWER SYBR Green Cells-to-Ct kit (Ambion). Quantitative PCR was performed to measure the expression levels of GUSB, TERT, GABPB1L, and GABPB2 as described below. All siRNAs were independently validated at 48 and 72 hours post-transfection for >50% knockdown of target transcript in all cell lines.

RT-qPCR~

Quantitative PCR was performed with POWER SYBR Green complete master mix (Life Technologies) to measure the expression levels of GUSB, TERT, GABPB1, GABPB1L, and GABPB2. Each sample was measured in triplicate on the Applied Biosystems 7900HT Fast Real-Time System. Melting curves were manually inspected to confirm PCR specificity. Relative expression levels were calculated by the deltaCT method against GUSB.

Cell Viability Assays—

Cell lines were seeded at a density of 5000 cells/mL in 96-well plates. At t=24, 48 and 96 hours post-seeding, MTS (Cell titer 96 aqueous MTS, Promega) was incubated for 2 hours at 37° C. in a ratio of 1:5 in media, according to manufacturer's instructions. Plate was read on the Bioplate Synergy 2 microplate reader at 490 nm. Cell proliferation of individual samples was calculated by normalizing absorbance to their corresponding absorbance at t=24 hours. Each time point was analyzed in triplicates.

Immunoblotting—

Immunoblotting for Cyclophilin B (loading control) and GABPB1 was performed using a rabbit anti-Cyclophilin B antibody PA1-027A (Pierce antibodies; 1:1000 dilution) and rabbit anti-GABPB1 antibody 12597-1-AP (Proteintech; 1:500 dilution) using the NuPAGE system (Thermofisher), according to the provider's instructions. Detection of primary bands was done using the Li-Cor goat anti-rabbit 680RD secondary antibody (1:15000 dilution) on the Li-Cor Odyssey Fc imaging system.

TCGA Data Analysis—

The collection of the data from The Cancer Genome Atlas (TCGA) (Network, C. G. A. R Comprehensive genomic characterization defines human glioblastoma genes and core pathways. *Nature* 455, 1061-1068 (2008)) was compliant with all applicable laws, regulations, and policies for the protection of human subjects, and necessary ethical approvals were obtained. Analysis of all data was done in R project version 3.3.2 (http://www.r-project.org/). Normalized RNA-seq expression data for GABP and TERT were downloaded along with clinical information from TCGA (level 3 normalized data, December 2015, http://itcga-data.nci.nih.gov/tcga/dataAccessMatrix.htm) for 143 glioblastoma (109 TERT-expressing and 34 TERT-deficient) samples, 49 oligodendroglioma (49 TERT promoter-mutant) samples, and 249 colorectal cancer (249 TERT-expressing) samples. TERT mutation status was obtained from Ceccarelli et al for all glioma samples (Ceccarelli et al. Molecular Profiling Reveals Biologically Discrete Subsets and Pathways of Progression in Diffuse Glioma. *Cell* 164, 550-563 (2016). GABP isoforms were analyzed for associations with TERT using Spearman's correlation. A linear trend-line was generated using the PCA orthogonal regression line.

In vivo Studies~

Immunocompromised, nude mice were injected with $3 \times 10^5$ DBTRG05-MG glioblastoma cells (C228T TERTp mutant) intracranially using a Hamilton syringe method and orthotopic tumors were allowed to grow until visible by live bioluminescence imaging (BLI). Once tumors achieved $1 \times 10^5$ photons/second size by BLI, mice were injected with either vehicle control (PBS) or LNA-ASO UTR1 via CED directly to the tumor mass. All mice were sacrificed 3 days post LNA injection and fresh tumor tissue was collected for RNA analysis.

Results

Figure 2A:
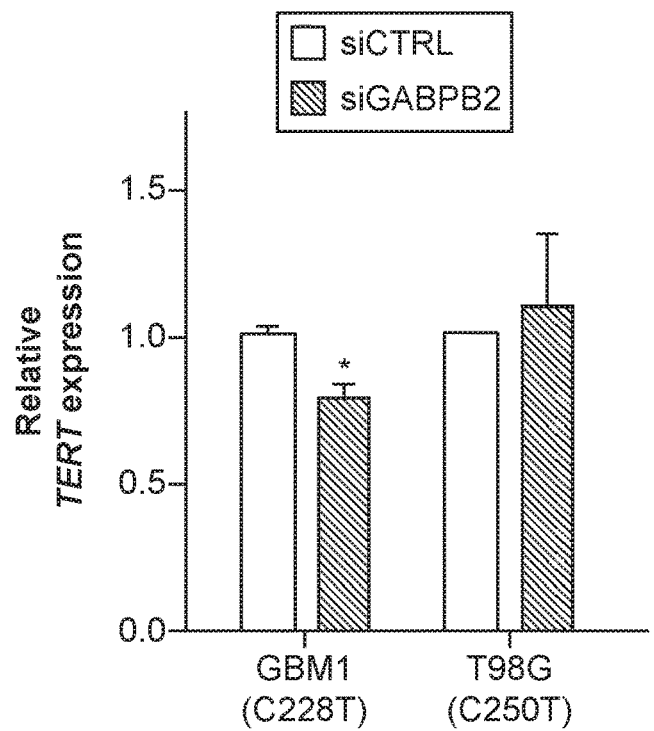
FIG. 2 shows that GABPB2 knockdown had little to no effect on mutant or wild-type TERT expression. TERT expression following siRNA-mediated knockdown of GABPB2 in (a) GBM1 and T98G or (b) HCT116 and HEK293T lines. *P<0.05, two-sided Student's t-test compared to siControl (siCTRL) in each respective line. Values are mean±S.D. of at least three independent experiments (two independent experiments for HCT116 lines).
Figure 2B:
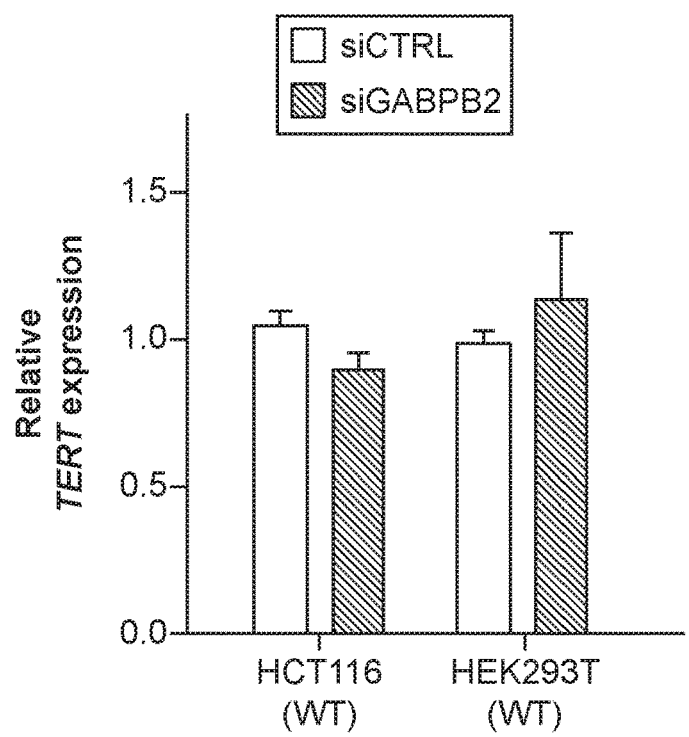
Figure 3A:
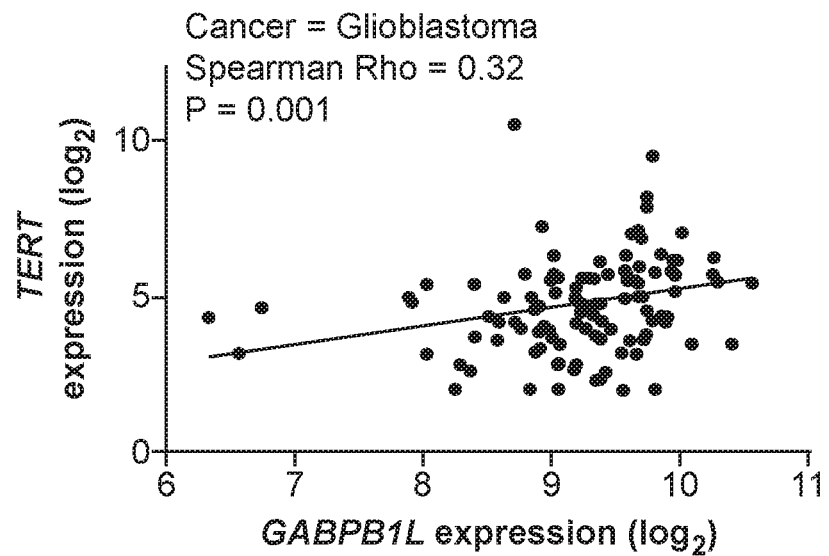
FIG. 3 shows that expression of the GABP tetramer-forming isoform GABPβ1L correlates with TERT expression in TERT promoter mutant glioma. (a-d) Correlation of GABPB1L or GABPB1S expression (log 2 normalized counts) versus TERT expression (log 2 normalized counts) from (a,b) 109 TERT-expressing GBMs or (c,d) 49 TERT promoter-mutant oligodendrogliomas. (e-h) Correlation of GABPB1L, or GABPB2 expression (log 2 normalized counts) versus TERT expression (log 2 normalized counts) from (e) 109 TERT-expressing GBMs, (f) 49 TERT promoter-mutant oligodendrogliomas, or (g-h) 262 TERT-expressing colorectal cancers. Grey line indicates trend line.
Figure 3B:
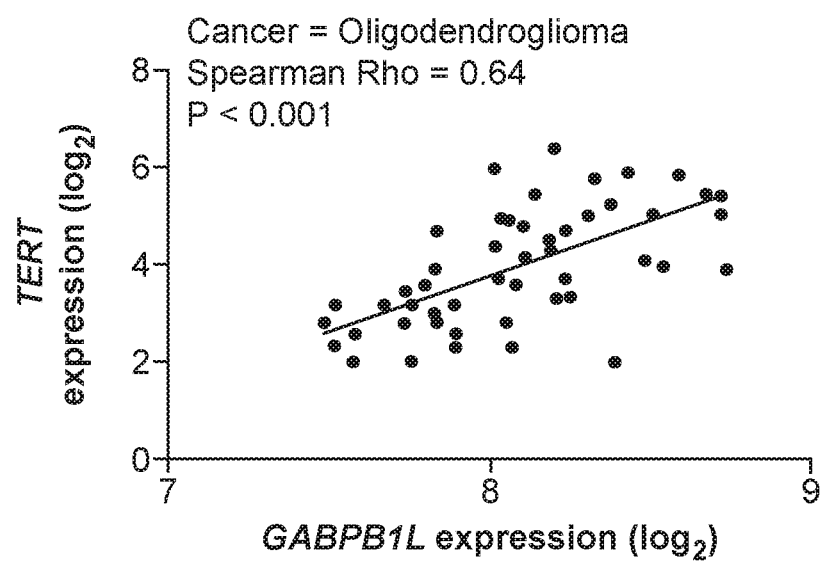
Figure 3C:
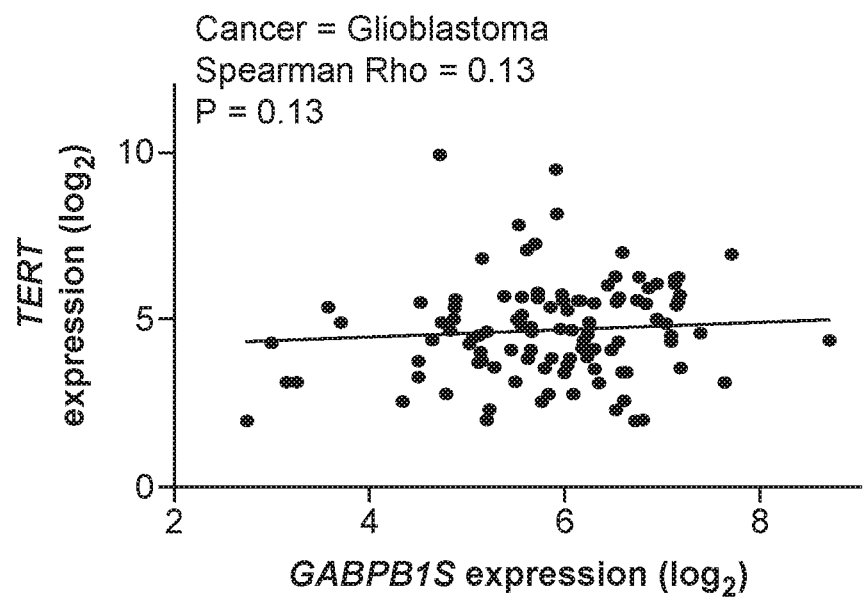
Figure 3D:
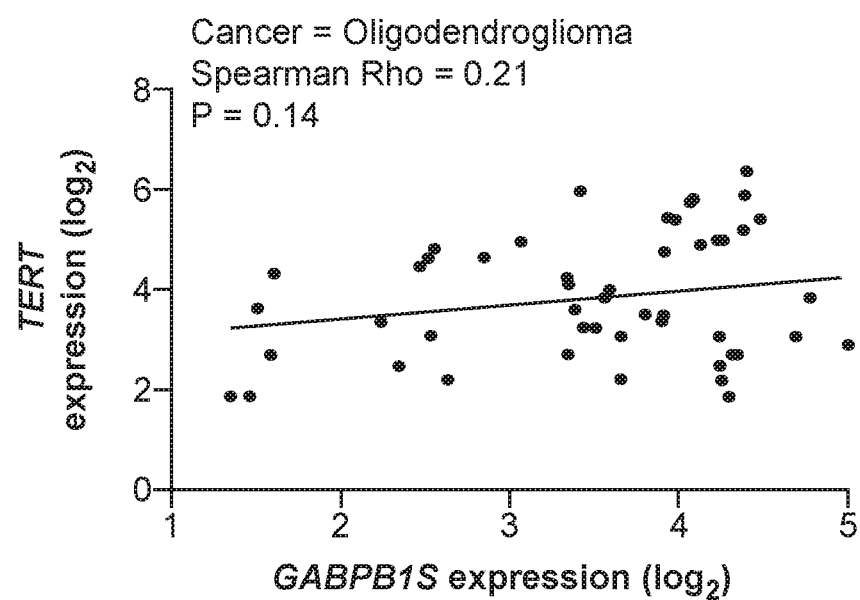
Figure 3E:
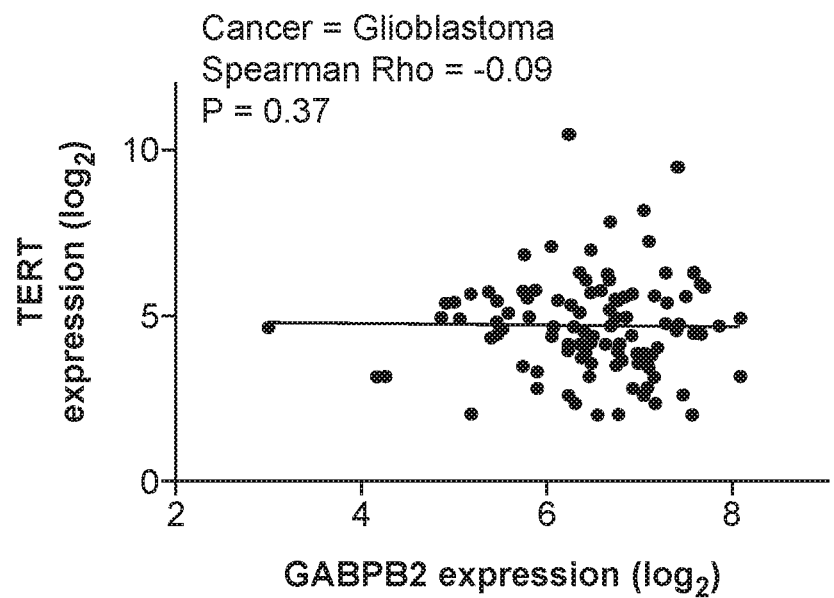
Figure 3F:
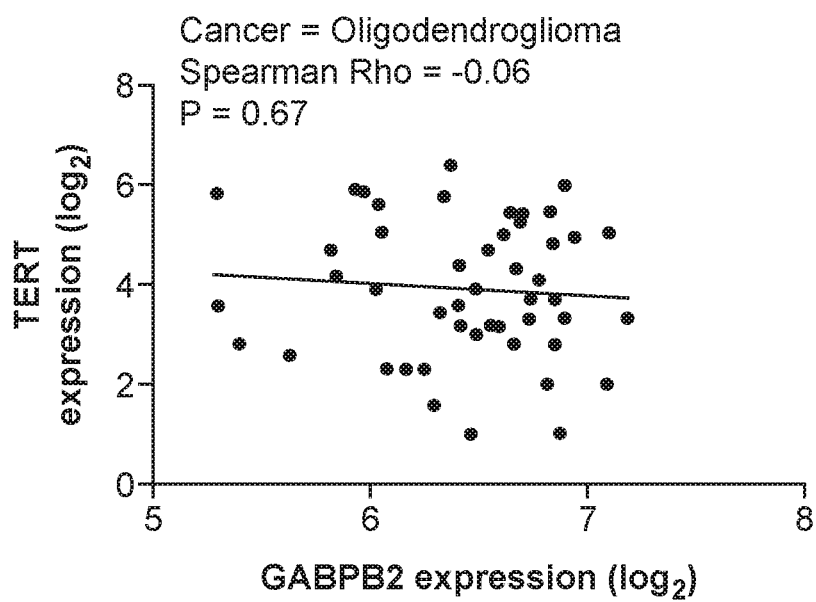
Figure 3G:
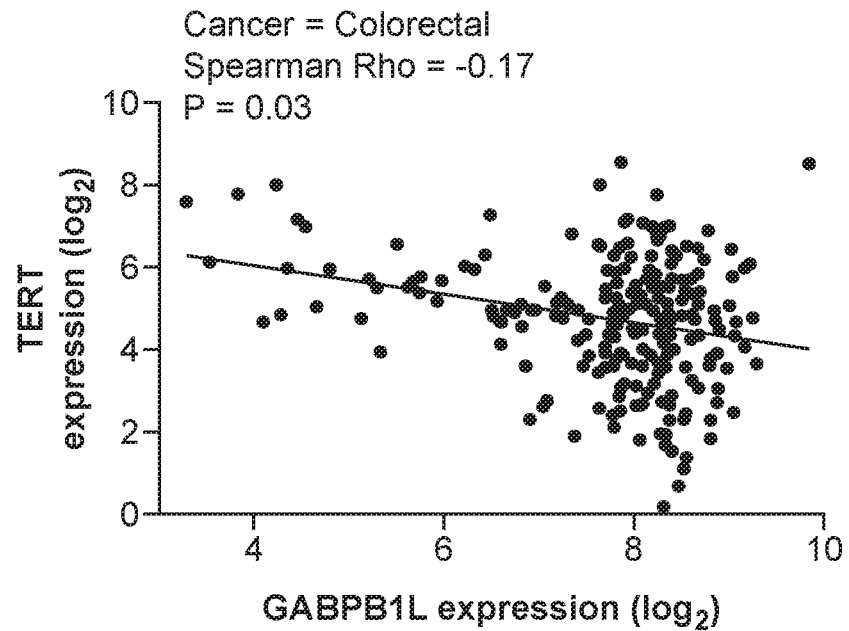
Figure 3H:
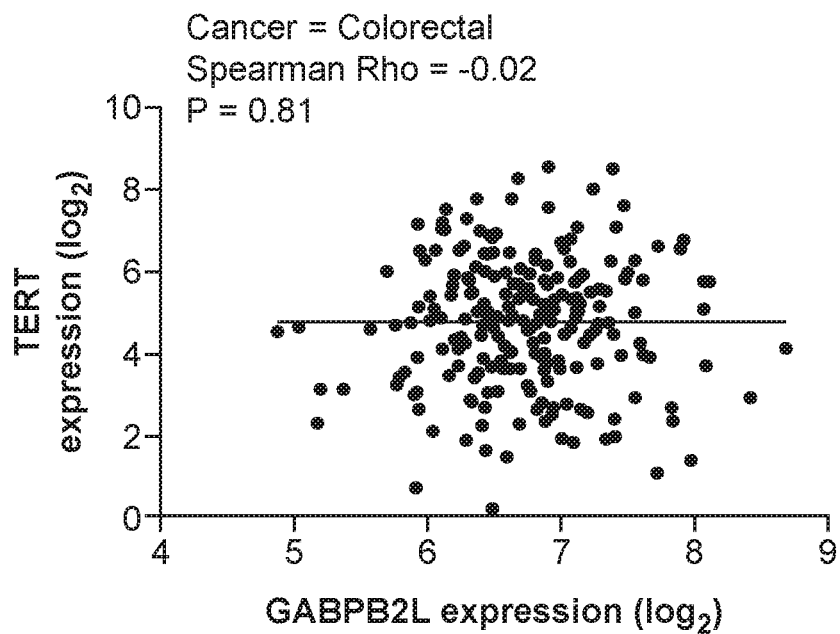

To determine if the GABP dimer-forming isoform (GABPβ1S) or the tetramer-forming isoforms (GABPβ1L and GABPβ2) regulate the mutant TERT promoter, siRNA-mediated knockdown of GABPβ1 and GABPβ2 was used in three TERT promoter mutant cell lines (GBM1 [C228T], T98G [C250T], OG1 [C228T]) and two TERT expressing, promoter wild-type cell lines (HCT116 and HEK293T). GBM1 and T98G are TERT promoter mutant primary GBM lines, and OG1 is a patient-derived TERT promoter mutant recurrent oligodendroglioma line. Knockdown of GABPβ1 significantly reduced TERT expression in all three TERT promoter mutant cell lines, but had limited effect in TERT promoter wild-type lines (as shown in FIG. 1). In contrast, siRNA-mediated knockdown of GABPβ2 had no appreciable effect on TERT expression irrespective of TERT promoter status (as shown in FIG. 2). Due to the possibility of the GABP tetramer binding to the mutant TERT promoter, expression of the tetramer-forming GABPB1L isoform was specifically looked for in this knockdown study and significant depletion of this isoform after siRNA-mediated knockdown in all three TERT promoter mutant cell lines was confirmed (FIG. 1).

This significant knockdown of GABPB1L led to testing of whether the expression of TERT correlates with GABPB1L expression in TERT promoter mutant GBMs and oligodendrogliomas. This analysis revealed a significant positive association between TERT and GABPB1L mRNA in both cancer types, but no significant correlation between TERT and GABPB1S or GABPB2 (FIG. 3) mRNA levels. Furthermore, analysis of GABP isoform and TERT expression data in the predominantly TERT promoter wild-type colorectal cancer revealed no positive correlation between TERT expression and GABPB1L or GABPB2 expression (FIG. 3). Taken together, these data supported that the GABP tetramer-forming isoform GABPβ1L was necessary for activation of the mutant TERT promoter, and that GABPB2 and GABPβ1S did not play a role in mutant TERT activation.

Next, designing an antisense oligonucleotide (ASO) to specifically target GABPB1L while leaving GABPB1S mRNA expression intact was performed. Additionally, Locked Nucleic Acid-ASOs (LNA-ASOs) was designed instead of research grade siRNA, as LNA-ASOs more closely resemble ASOs that can be administered as therapeutics. LNA-ASOs are resistant to endonucleases due to their Locked-Nucleic acid modified ribose ring, thus increasing their stability in serum (Braasch & Corey, Locked nucleic acid (LNA): fine-tuning the recognition of DNA and RNA. *Chem. Biol.* 8, 1-7 (2001)). They can cross cell membranes without assistance from delivery agents, through a process called gymnnosis (Stein et al. Efficient gene silencing by delivery of locked nucleic acid antisense oligonucleotides, unassisted by transfection reagents. *Nucleic Acids Res.* 38, e3-e3 (2009); and Zhang et al. Down-modulation of cancer targets using locked nucleic acid (LNA)-based antisense oligonucleotides without transfection. *Gene Ther.* 18, 326-333 (2010)). Due to these advances, chemically modified ASOs are in phase three clinical trials for multiple human diseases including cancer (Rigo et al. Pharmacology of a Central Nervous System Delivered 2'-O-Methoxyethyl-Modified Survival of Motor Neuron Splicing Oligonucleotide in Mice and Nonhuman Primates. J. Pharmacol. Exp. Ther. 350, 46-55 (2014); Miller et al. An antisense oligonucleotide against SOD1 delivered intrathecally for patients with SOD1 familial amyotrophic lateral sclerosis: A phase 1, randomised, first-in-man study. Lancet Neurol. 12, 435-442 (2013)).

Figure 4:
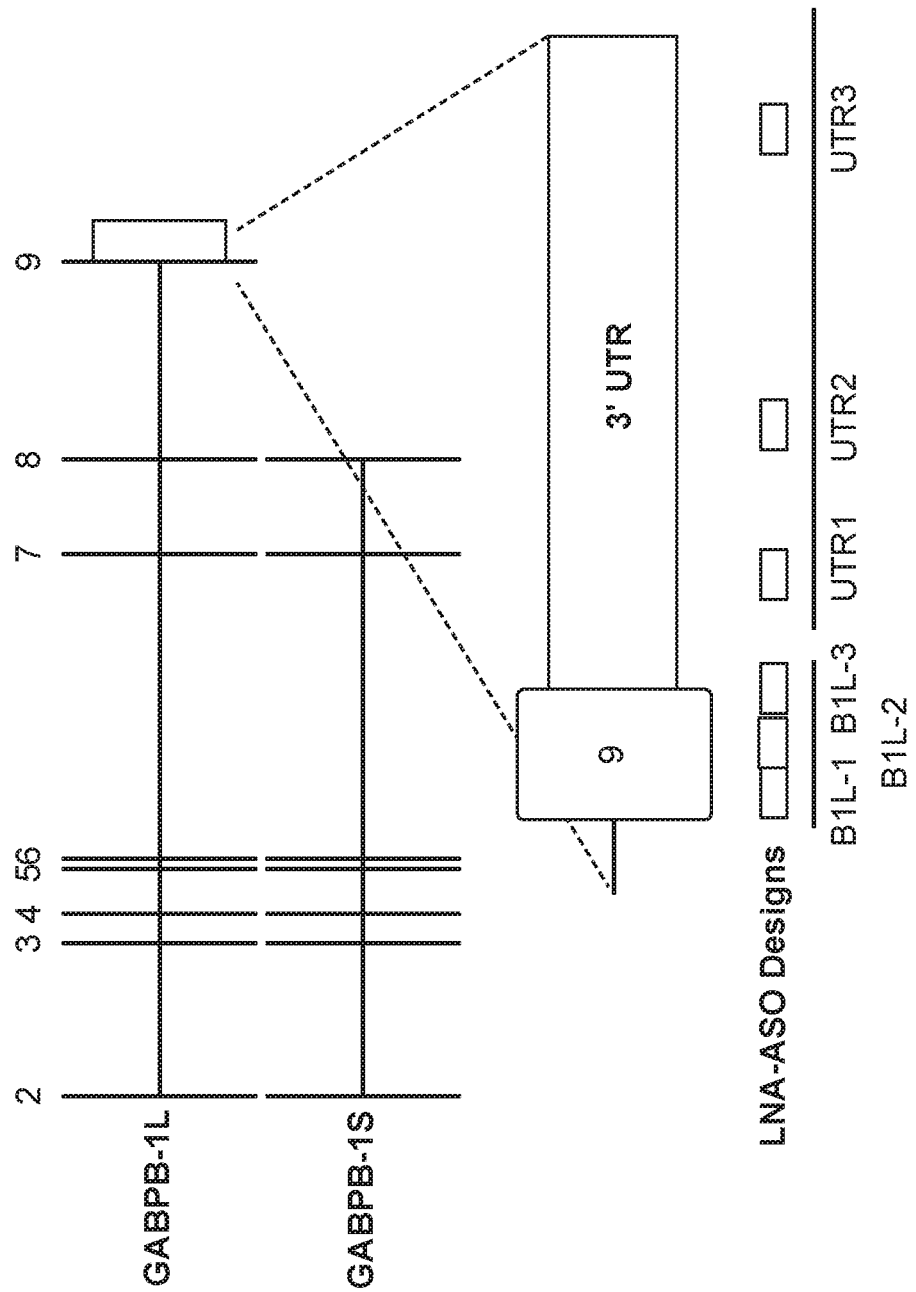
FIG. 4 shows LNA-ASO designed to target either exon 9 or the UTR of GABPB1L. Exon structure for GABPB1 S and GABPB1L. Inset shows the location of the six LNA-ASOs that were designed to hybridize to either the 9th exon or UTR of GABPB1L.

Six LNA-ASOs specifically targeting GABPB1L through exon 9 or its 3' UTR (FIG. 4) were designed and ordered from Exiqon (LNA-ASO B1L-1, B1L-2, B1L-3, UTR1, UTR2, UTR3—as shown in Table 1 below).

TABLE 1

| Name | Antisense sequence | Sense sequences |
|---|---|---|
| B1L-1 | TAGGAGCTGCTGTCGA (SEQ ID NO: 10) | TCGACAGCAGCTCCTA (SEQ ID NO: 4) |
| B1L-2 | AACTTCTGTCTGTAGG (SEQ ID NO: 11) | CCTACAGACAGAAGTT (SEQ ID NO: 5) |
| B1L-3 | TTAAACAGCTTCTTTA (SEQ ID NO: 12) | TAAAGAAGCTGTTTAA (SEQ ID NO: 6) |
| UTR1 | CTAACCAACAACGATC (SEQ ID NO: 7) | GATCGTTGTTGGTTAG (SEQ ID NO: 1) |
| UTR2 | TGAACAGTCTGCCAGT (SEQ ID NO: 8) | ACTGGCAGACTGTTCA (SEQ ID NO: 2) |
| UTR3 | CAGTCCACCATAATTA (SEQ ID NO: 9) | TAATTATGGTGGACTG (SEQ ID NO: 3) |

Figure 5A:
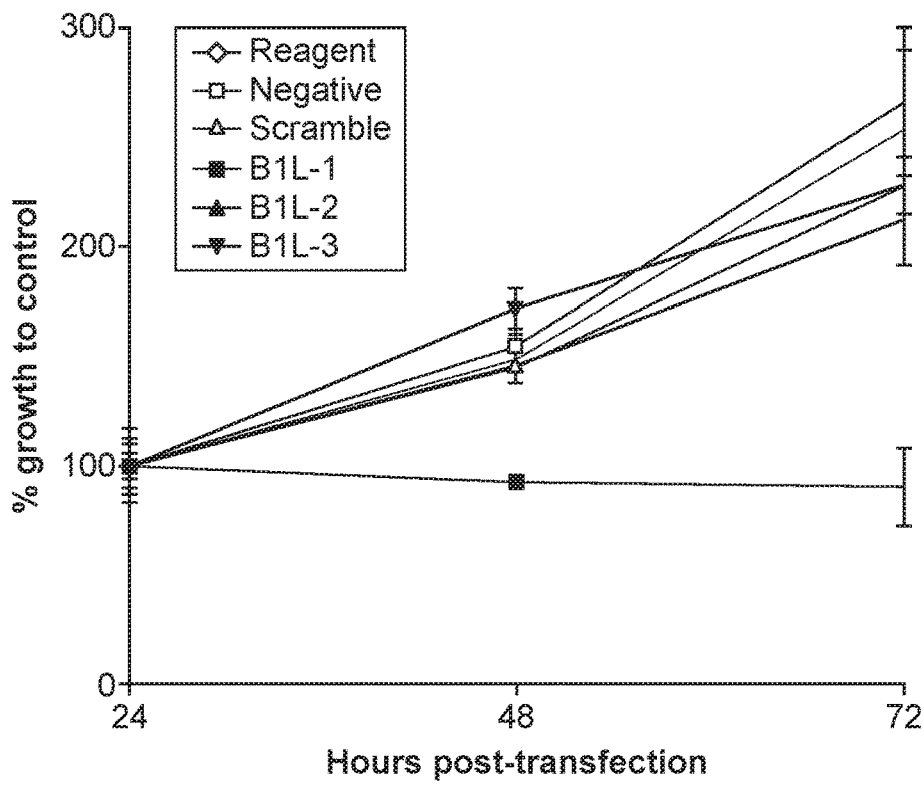
FIG. 5 shows that GABPB1L targeted LNA-ASOs had varying degrees of acute cell toxicity. Patient derived glioblastoma cells (GBM1) were transfected with nothing, transfection reagent only, a scramble control, or various GABPB1L targeted LNA-ASO sequences and cell growth was measure at 48 and 72 hr by MTS assay.
Figure 5B:
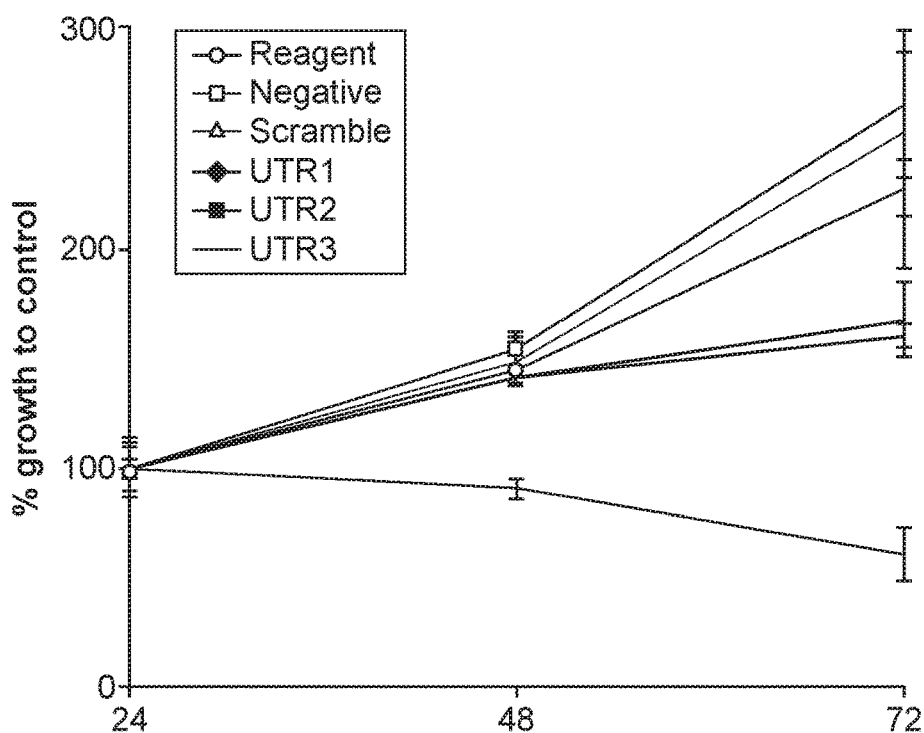
Figure 6:
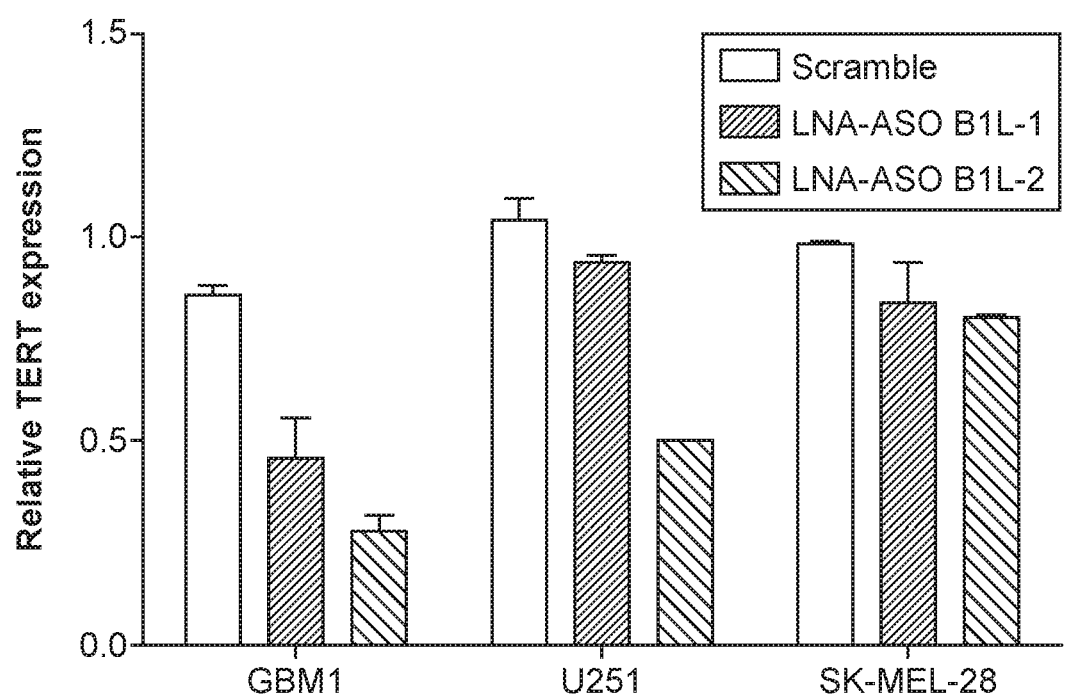
FIG. 6 shows that GABPB1L targeted LNA-ASOs reduced TERT expression in a TERT promoter mutant dependent manner. TERT expression following LNA-ASO mediated knockdown of GABPB1L via either LNA-ASO B1L-1 or B1L-2 in TERT promoter mutant cells (GBM1, U251) or TERT wild-type cells (SK-MEL-28).
Figure 7:
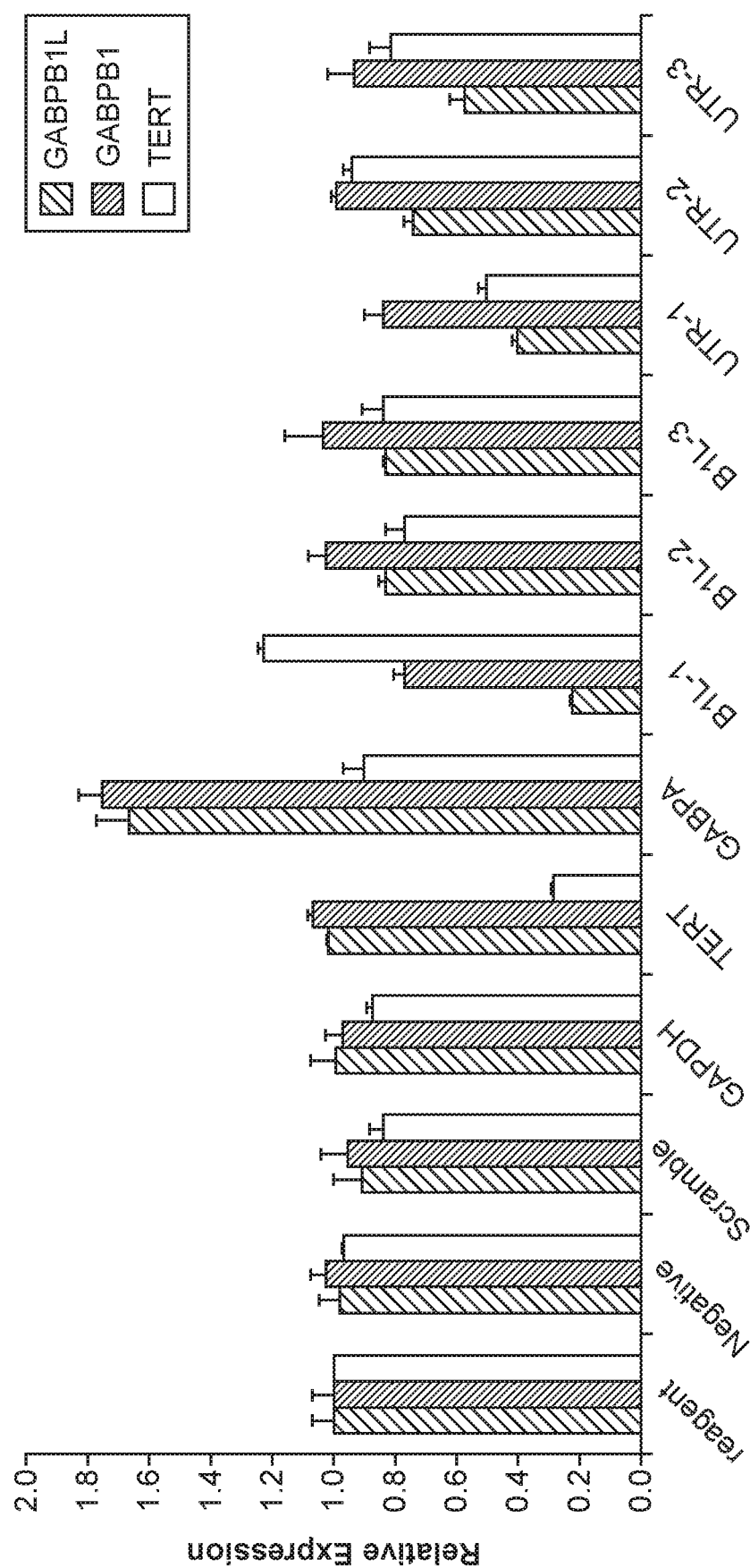
FIG. 7 shows that GABPB1L targeted LNA-ASOs specifically knocked down GABPB1L transcription while leaving overall GABPB1 transcript levels intact. Expression of total GABPB1, GABPB1L, and TERT following LNA-ASO transfection is shown. The transfected LNA-ASO is listed on the x-axis. A GAPDH and Scramble LNA-ASO were used as negative controls and TART and GABPA-targeted LNA-ASOs were used as positive controls.
Figure 8:
FIG. 8 shows that LNA-ASO UTR1 reduced the protein expression of GABPB1L but not GABPB1S. Protein expression in the HCC cell line SNU-423 following LNA-ASO UTR1 knockdown of GABPB1L is shown. The protein bands are quantified on the right bar graph.

As LNA-ASOs can be non-specifically toxic to cells, their acute cell toxicity was first tested via an MTS assay. (as shown in FIG. 5). LNA-ASOs BIL-1 and UTR3 were found to be acutely toxic, while LNA-ASOs UTR1 and UTR2 were found to have mild toxicity. Next, whether GABPB1L-targeted LNA-ASOs could reduce TERT expression in a TERT promoter mutant dependent manner was tested. LNA-ASO B1L-1 and B1L-2 were transfected into two TERTp mutant cell lines (GBM1 and U251), and one TERTp wild-type cell line (SK-MEL-28). Interestingly, LNA-ASO B1L-2 was able to significantly reduce TERT expression in both TERTp mutant lines while not having a significant effect in the wild-type line (FIG. 6). Finally, whether the LNA-ASOs were specifically silencing the GABPB1L isoform while leaving the GABPB1S isoform intact was confirmed. FIG. 7 shows that LNA-ASO BIL-1 and UTR1 were able to reduce GABPB1L levels by more than 50% while leaving total GABPB1 levels altered less than 20%. Additionally, LNA-ASO UTR1 also reduced TERT expression by −50%. Due to the acute toxicity previously observed with LNA-ASO BIL-1, it was decided to focus on LNA-ASO UTR1 for further studies. The ability of LNA-ASO UTR1 to specifically silence GABPB1L protein by western blot was also measured. FIG. 8 shows that transfection of LNA-ASO UTR1 into the HCC cell cline SNU-423 results in 50% reduction of GABPB1L expression, while GABPB1S actually increases by 20%. These data support the design of an ASO to specifically silence GABPB1L and concomitantly reduce TERT expression from the mutant TERT promoter in vitro.

Figure 9A:
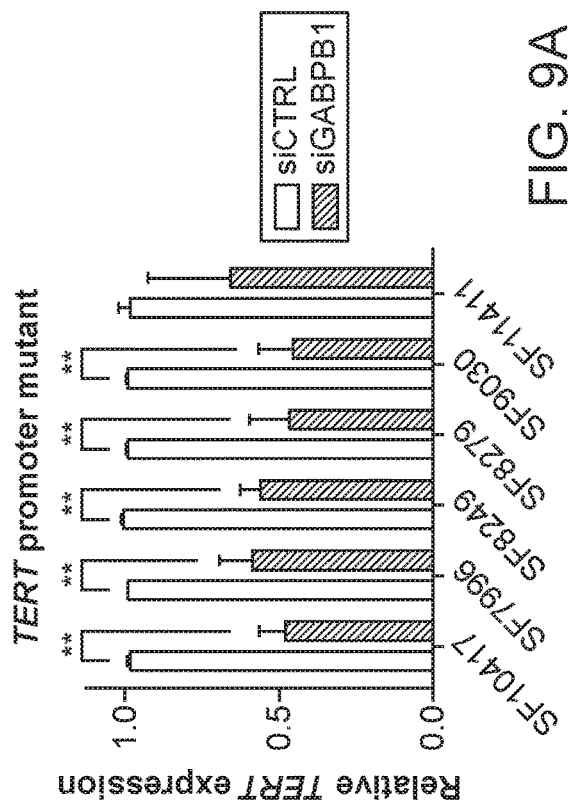
FIG. 9 shows that knockdown of GABPB1 via siRNA reduces TERT expression in TERT promoter mutant patient-derived glioma cultures, but not brain-derived TERT promoter wild-type cultures. TERT (a,b) or GABPB1L (c,d) expression measured via qPCR 72 hours post-siRNA knockdown of GABPB1 in TERT promoter mutant glioma cultures (a,c) or brain-derived TERT promoter wild-type cultures (b,d). NHAPC5=Normal human astrocytes post-crisis clone 5. LNI 8=TERT promoter wild-type glioblastoma. hNPCs=iPSC-derived human Neural Precursor Cells.
Figure 9B:
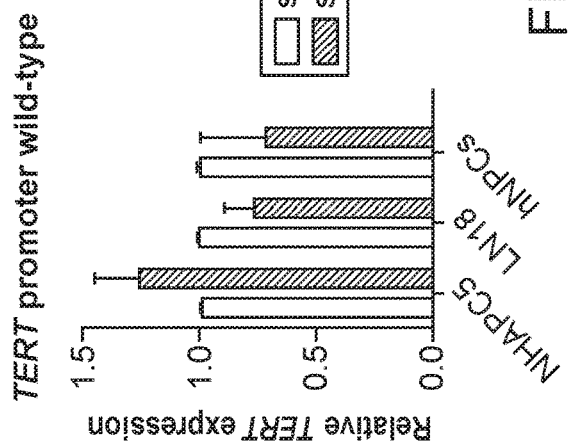
Figure 9C:
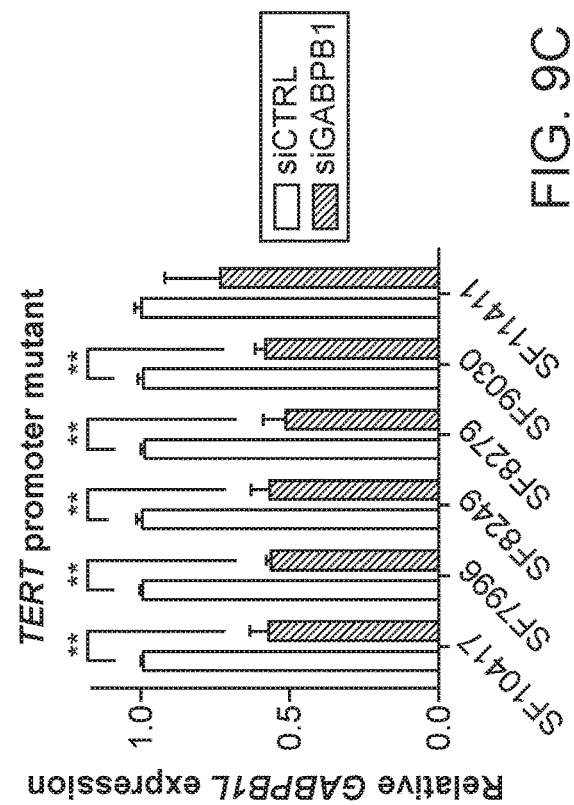
Figure 9D:
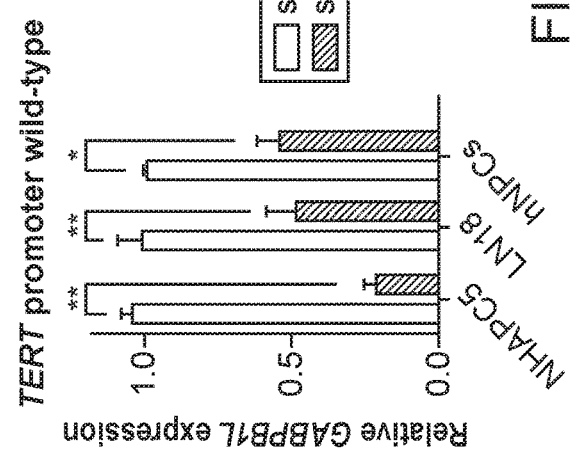
Figure 10A:
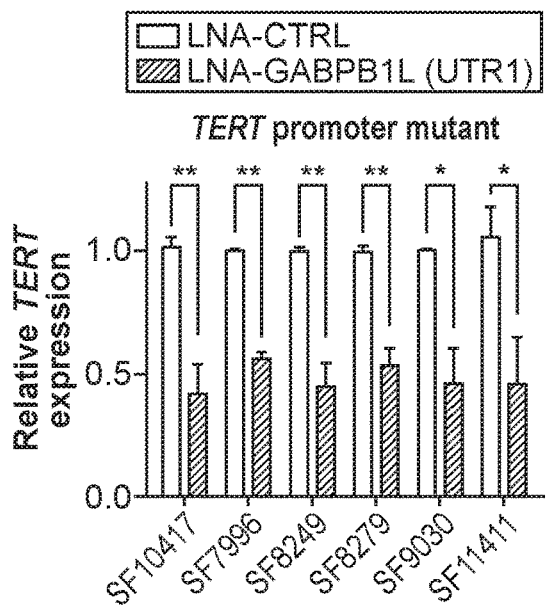
FIG. 10 shows that knockdown of GABPB1L via LNA-ASO UTR1 reduces TERT expression in TERT promoter mutant patient-derived glioma cultures, but not brain-derived TERT promoter wild-type cultures. TFRT (a,b) or GABPB1L and GARBPBIS (c,d) expression measured via qPCR 72 hours post-knockdown of GARBPBIL using the UTR1 LNA-ASO in TERT promoter mutant glioma cultures (a,c) or brain-derived TERT promoter wild-type cultures (b,d). NHAPC5=Normal human astrocytes post-crisis clone 5. LN18=TERT promoter wild-type glioblastoma. hNPCs=iPSC-derived human Neural Precursor Cells.
Figure 10B:
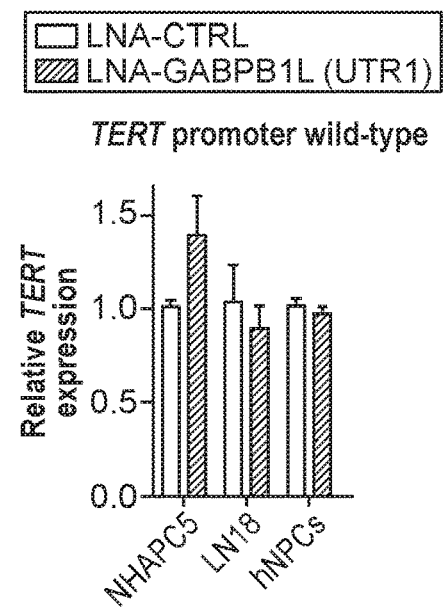
Figure 10C:
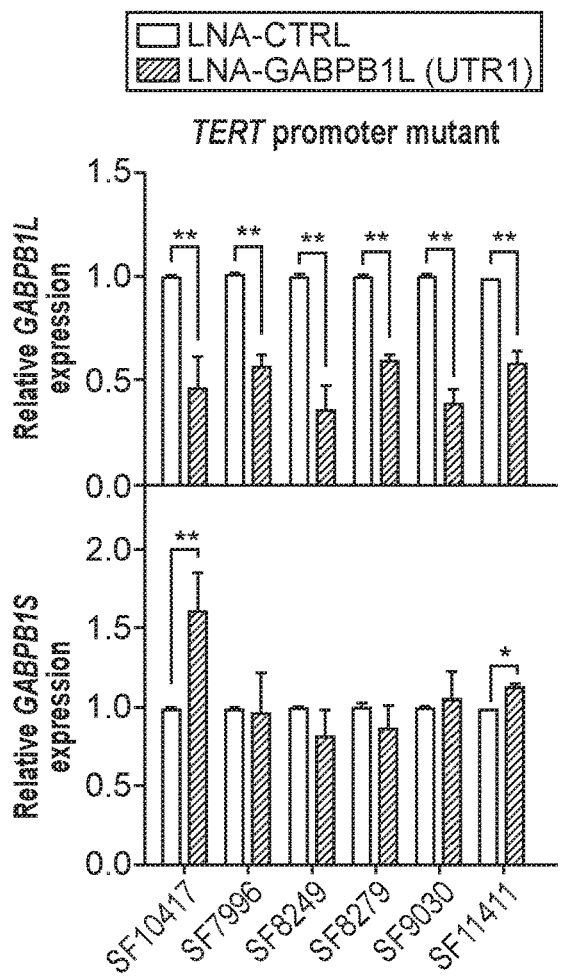

To further validate the effects of GABPB1L knockdown on TERT expression in clinically relevant models of glioma, six primary cell cultures derived from patients with TERT promoter mutant anaplastic oligodendroglioma (SF10471) or glioblastoma (SF7996, SF8249, SF8279, SF9030, and SF11411) were utilized. In addition to these patient-derived cultures, three new TERT promoter wild-type lines were included as controls for TERT promoter mutation specificity of GABPB1L knockdown. These TERT promoter wild-type lines are the human astrocyte-derived line NHAPC5, the iPSC-derived human neural precursor cell line hNPCs, and the glioblastoma-derived line LN18. Both the siRNA pool targeting GABPB1 and the LNA-ASO UTR1 (SEQ ID NO: 7) targeting GABPB1L significantly reduced TERT expression across the panel of TERT promoter mutant patient-derived cultures (FIGS. 9a and 10a) while having no effect on the TERT promoter wild-type cultures (FIGS. 9b and 10b).

Figure 10D:
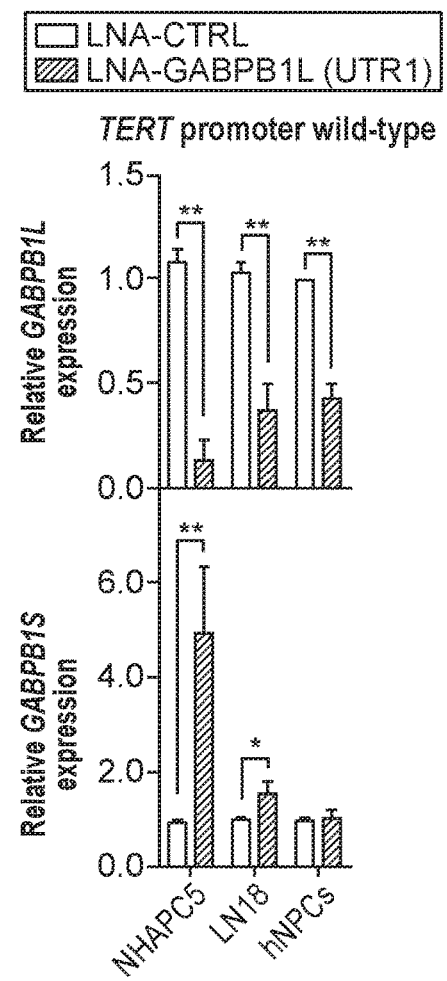

Both the GABPB1-targeting siRNA pool and the GABPB1L-targeting UTR1 LNA-ASO significantly depleted GABPB1L mRNA levels (FIGS. 9c, 9d, 10c, and 10d). Additionally, the UTR1 LNA-ASO did not reduce GABPB1S levels in any culture assayed (FIG. 10d). These data further validate the specificity of inhibiting GABPB1L to reduce TERT expression in TERT promoter mutant glioma as TERT reduction was exclusive to the clinically relevant TERT promoter mutant patient-derived glioma lines and was not observed in the brain-derived TERT promoter wild-type lines.

A screen for splice switching LNA-ASOs (ssLNAs) that inhibit GABPB1L in TERT promoter mutant glioma was also performed. The target region encompassed the entirety of GABPB1 exon 9 (GABPB1L-specific) and the adjacent upstream intronic region and downstream 3' UTR. The GABPB1L-targeting LNA-ASO UTR1 reduces GABPB1L levels through an RNase H-dependent degradation mechanism. To minimize the off-target effects associated with RNase H-activating LNA-ASOs, a library of non-degradatory splice-switching LNA-ASOs (ssLNAs) was screened for inhibition of GABPB1L splicing. In brief, these ssLNAs occlude splice recognition sites on the GABPB1 pre-mRNA to prevent maturation of the GABPB1L mRNA without eliciting an RNase H response. To prevent RNase H activation, ssLNAs alternate LNA-modified ribonucleotides and unmodified deoxyribonucleotides along the entirety of the phosphorothioate antisense oligonucleotide backbone. Using ssLNAs to inhibit splicing of GABPB1L is thus a novel and unique approach to deplete TERT in TERT promoter mutant glioma.

Figure 11:
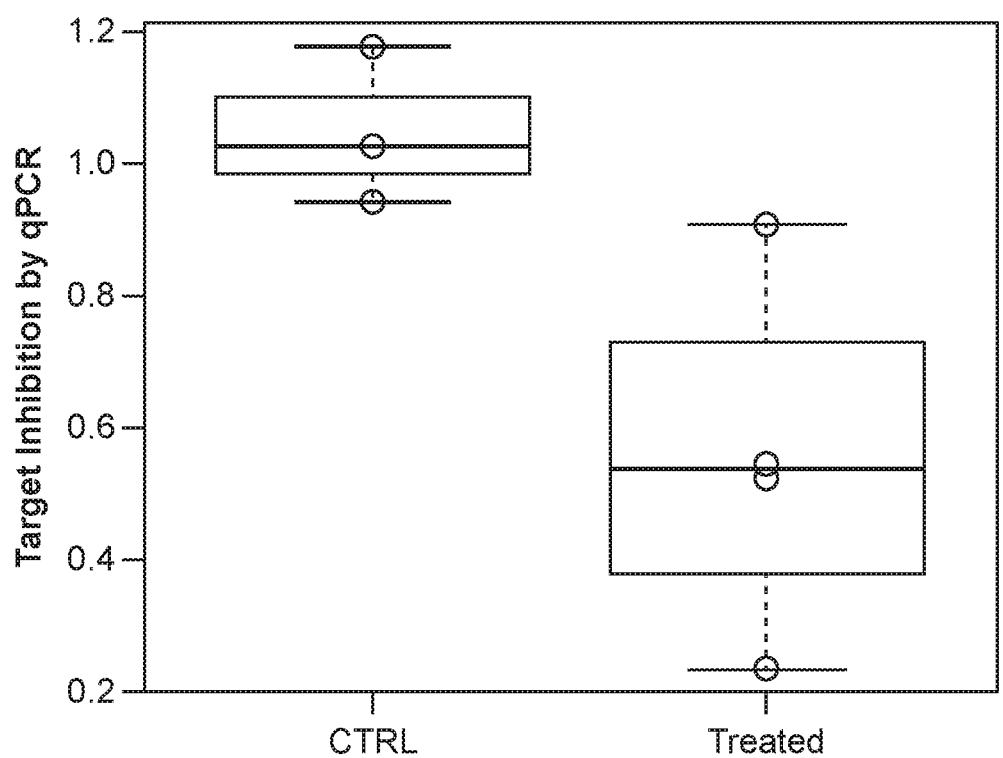
FIG. 11 shows that LNA-ASO UTR1 reduced GABPB1L in a GBM xenograft in-vivo model. mRNA expression of GABPB1L in DBTRG05-MG grown intracranially in mice following injection of LNA-ASO UTR1 is shown. Mice were injected with either vehicle control (n=3) or LNA-ASO UTR1 (n=4) and sacrificed three days post-injection. RNA was isolated from the tumors and GABPB1L was measured via RT-qPCR.

The disclosure also describes achieving a similar level of GABPB1L inhibition through in vivo administration of a GABPB1L-targeted ASO, in the absence of transfection reagent. A pilot experiment using 6 mice harboring intracranial xenografts of DBTRG05-MG GBM cells was performed. Once the tumor size became detectable by live bioluminescence imaging, the orthotopic tumors were injected with either LNA-ASO UTR1 (n=4) or vehicle control (n=3). Mice were sacrificed three days after LNA-ASO injection and the tumors were harvested for RNA isolation and RT-qPCR analysis. FIG. 11 shows that the tumors in the treatment group had significantly reduced GABPB1L mRNA expression compared to the control group. Thus, this shows an LNA-ASO that can be delivered without a delivery reagent in vivo to specifically target the GABPB1L isoform in TERT promoter mutant tumors The studies provided herein showed that GABPB1L is the only GABPB isoform required to activate the mutant TERT promoter, and that it is possible to design a chemically modified ASO to silence GABPB1L, reduce TERT expression, and leave GABP dimer function intact. These data support methods of targeting GABPB1L to reduce telomerase in TERT promoter mutant cancers. Genetic knockout of either GABPA or total GABPB1 (GABPB1S and GABPB1L), results in embryonic lethality in mice, indicating that total GABP function is vital for healthy cell function (31,37). This lethality phenotype significantly limits the potential to block total GABP function as a strategy to therapeutically intervene with mutant TERT activation. In addition, both GABPB1L and GABPB2 can form the GABP heterotetramer highlighting the potential for functional redundancy in the target genes they regulate(28). However, as shown herein, there is striking specificity for the GABPB1L isoform, but not the GABPB2 isoform, to regulate mutant TERT expression. Thus, a GABPB1L-targeted therapeutic will achieve potent TERT reduction without creating the severe patient toxicities we would expect from total GABP functional inhibition.

Although specific inhibition of GABPB1L via small molecules is possible, this may prove challenging, as the only difference between GABPB1S and GABPB1L is the LZD encoded by exon 9. In contrast, ASOs are well suited to this type of target as they can be specifically designed to inhibit one isoform but not the other. LNA-ASOs were tested to prove that these next-generation ASOs could be used to target GABPB1L in vivo. The Locked Nucleic Acid modification (where the ribose ring is connected by a methylene bridge between the 2'-O and 4'-C atoms), allows for smaller sequences to attain the necessary binding affinities to hybridize to their targets at physiological temperature and pH. It also renders the ASOs more resistant to endonuclease degradation in the serum (Braasch & Corey). Unassisted cell uptake (termed gymnosis) has also been documented with LNA-ASOs, though the exact mechanism has yet to be elucidated (Stein et al.; and Zhang et al.). Thus, chemically modified ASOs like LNA-ASOs provide a viable therapeutic modality that can effectively block GABPB1L function in cancer patients. There are also other modified oligonucleotide chemistries that have similar or superior effects on ASOs than LNAs. These include, Bridged Nucleic acids (BNAs), peptide nucleic acids (PNAs), ethylene-bridged nucleic acids (ENAs), 2'-O-methyl (2-OMe) modified RNA, 2'-O-methoxyethyl (2-MOE) modified RNA, hexitol nucleic acids, and oligonucleotides with Phosphorothioated backbones (Thomas et al. Antitumor Effects of EGFR Antisense Guanidine-Based Peptide Nucleic Acids in Cancer Models. 8, 345-352 (2013); Topics, C. Biological and Pharmaceutical Aspects of Nucleic Acids Chemistry 2-O, 4-C-Ethylene-Bridged Nucleic Acids (ENA™) as Next-Generation Antisense and Antigene Agents. 27, 453-456 (2004); Kang et al. Inhibition of MDRl gene expression by chimeric HNA antisense oligonucleotides. 32, 46-51 (2004); Rahman et al. EXCELLENT HYBRIDIZING AND NUCLEASE RESISTANCE PROFILES. 1625-1628 (2007). doi: 10.1080/15257770701548980; Technology, A. Development of Bridged Nucleic Acid Analogues for Antigene Technology. 52, 1399-1404 (2004); and Imanishi & Obika. BNAs: novel nucleic acid analogs with a bridged sugar moiety. 1653-1659 (2002)). Creating an ASO with one or multiple of these chemical modifications can be used to achieving stabile GABPB1L inhibition in patients while minimizing non-specific toxicities).

In some embodiments, in addition to stabilizing backbone chemical modifications, a GABPB1L targeted ASO is coupled with a delivery technology to further increase its efficacy, improve tissue distribution, and reduce toxicity. Though the ability to achieve GABPB1L knockdown in vivo through direct delivery into tumor tissue has been demonstrated herein, many groups, encapsulating ASOs in nanoparticles (NPs) can increase their effectiveness (Zatsepin & Koteliansky, Lipid nanoparticles for targeted siRNA delivery—going from bench to bedside. Int J Nanomedicine. 11, 3077-3086 (2016)). An alternative method to NPs is to chemically conjugate an ASO to a cell- or tissue-targeting ligand such as an antibody or a ligand for a cell surface receptor (Juliano, R L. The delivery of therapeutic oligonucleotides. Nucleic Acids Res. 44, 6518-6548 (2016); and Layek & Singh, J. Cell penetrating peptide conjugated chitosan for enhanced delivery of nucleic acid. International Journal of Molecular Sciences 16, 28912-28930 (2015)). Doing so can increase the effective ASO concentration at the tissue type harboring the resident tumor. In some embodiments, this is a component of ASO based GABPB1L targeted therapy.

Six LNA-ASOs designed to specifically inhibit the mRNA of GABPB1L have been synthesized. Although decreased TERT mRNA expression was achieved with several LNA-ASOs, one of these six (UTR1) was able to achieve significant GABPB1L knockdown and concomitantly reduced TERT mRNA expression. Any ASO which targets the intron between exon eight and nine of GABPB1, any part of exon nine, or the GABPB1L-specific 3' UTR could be used to silence GABPB1L while leaving GABPB1S translation intact. The optimal GABPB1L targeted ASO will depend on the chemical modifications used as well as their position in the ASO sequence, which can be determined based on routine experimentation.

Finally, as disclosed herein, the therapeutic applications of a GABPB1L targeted ASO applies to any cancer indication harboring TERT promoter mutations. This includes 83% of glioblastoma, 71% of melanoma, 66% of bladder cancer, and 47% of hepatocellular carcinoma. These mutations have now been found to exist in over 50 distinct cancer types, highlighting the significant need for the disclosed therapies. The data provided herein proves the ability for inhibiting GABPB1L translation to block mutant TERT activation while leaving GABP dimer function intact, thus treating a TERT promoter mutant cancer.

Publications cited herein and the material for which they are cited are hereby specifically incorporated by reference in their entireties. A number of embodiments have been described. Nevertheless, it will be understood that various modifications may be made. Accordingly, other embodiments are within the scope of the claims.

GABPB1L mRNA Sequences mRNA sequence comprising exon 9 and the 3' UTR of GABPB1L (SEQ ID NO: 13)

```
CAGAAATAGAAGAGAGAAGCTCTTCAGAAACAGCTGGATGAAGCAAATC
GAGAAGCACAAAAATATCGACAGCAGCTCCTAAAGAAAGAACAGGAAGCAG
AGGCCTACAGACAGAAGTTGGAAGCTATGACTCGTCTTCAGACTAATAAAG
AAGCTGTTTAATTGAAATGAACATGTAGTTTGATTTTACTTTTGGTCAAGA
AAGAATACAATCTTGAACTGTACACAACAAAGGTACAGCCATGGGAATACA
GAATGATAGAAGAGACTACAGATGGATAATTGGACTTAAGCCATGAGCTCT
GAGTTCTTGTAACATAAAACTTTACTTTAGAAGTTGTGAAATGTATTTAAA
ACTGAATTCTGTAAATAGTTTTTTTTTTTTACAGTTCCAAATGAGTTGAT
AAAGATTGTTGAAGAGATCCAAAACCAGAATAAGCCACTGTTTTTGTGAAT
TCTTTTTGATTTTAGTACAAACCTTAATTTCTCAGAAACGGAACAGTTTTA
AGGGTGATCGTTGTTGGTTAGGCCAAATGTTGTGTAATAATTATGGTGGAC
TGATGCTGGAATTACTCCTGTAGGTATAAACCTCTGTATGAAGAGAAGATT
```

| GABPB1L mRNA Sequences |
|---|
| TCTCCCAGGAAATCTTTGTACAGCTTTAAGTTGTGTCAGATTCTCTGAAAA |
| CATTTTTTAGAAAGCAAAATTTTTATATTTGTTCAATTTCAGCTATACCCA |
| AGTAGATTTACATGTATATGAAGCAAATATTTTTAAAAATTTCTGTTTGTA |
| CATATTCTGCATGTTTTATAATTTCAAATGCATCACTTACATAGGTATTT |
| CTCCCACAGAAATGATGAAAGTGACCAGAAAAAACAAAAACAAAACCCCT |
| TTACTCTGTAGGTCATTGAAACGAAGTAAGCTGGCAGCTGGTTTTATTGGA |
| ATGACAGTGTTCTCGGAAGGAGCAGCCTACAAGATAACTTGAATTTGCCAA |
| TTCTGCAAAATCTGTGCTTTTTTGAAAATTTAAGAGTGGGGACGTGAAACT |
| GTATTCTGTGCCTTCCATCATGATTTCCACATGAAAGCACTTTAAGGCACT |
| GATTTTAAGATAATGTTTTTGGAAAACCCAATGCATATGGGTTTCTGAAAT |
| ATTTTATGGACTTATTTCTCCCCAGGAAATGATTCTTACGGAAAAAATTGC |
| TTTTGTATGTAGAACAGGAACTTTTTGTATTACAGTGATGCAATAGACATG |
| TCTAATGAACTTCTACTTTTCCTTTTGAAAGCTCAGTGTCTGTGCTATGAC |
| TTGCTCTCATCACAATATTGTTGAATTCCACAATGTATGGACATTAAACAC |
| TGGCAGACTGTTCACTTTTTCTTTTTTTTTTGGTAAAATATTACTTCAA |
| ACCCCTTTTTCTTGCTTTATTTTTCAGTGTTTTATTGCTTTATGAACTGTT |
| TAACCCTGAAATCCCTCTAGGTTATCTATACTGTATAAAAAAGCAATTACC |
| CTTAALACTGTACTCTGGCCTACTTTTCTATTTTGCAATTAAATATCTTTT |
| TCACATATGTTCATTGTAGACTTATGTTTTATCACATCTTATTAACACAT |
| TAAAAATGTTATCCTACTGCA | mRNA sequence of the 3' UTR of GABPB1L
(SEQ ID NO: 14)
TTGAAATGAACATGTAGTTTGATTTTACTTTTGGTCAAGAAAGAATACAAT
CTTGAACTGTACACAACAAAGGTACAGCCATGGGAATACAGAATGATAGAA
GAGACTACAGATGGATAATTGGACTTAAGCCATGAGCTCTGAGTTCTTGTA
ACATAAAACTTTACTTTAGAAGTTGTGAAATGTATTTAAAACTGAATTCTG
TAAATAGTTTTTTTTTTTTTACAGTTCCAAATGAGTTGATAAAGATTGTTG
AAGAGATCCAAAACCAGAATAAGCCACTGTTTTTGTGAATTCTTTTTGATT

| GABPB1L mRNA Sequences |
|---|
| TTAGTACAAACCTTAATTTCTCAGAAACGGAACAGTTTTAAGGGTGATCGT |
| TGTTGGTTAGGCCAAATGTTGTGTAATAATTATGGTGGACTGATGCTGGAA |
| TTACTCCTGTAGGTATAAACCTCTGTATGAAGAGAAGATTTCTCCCAGGAA |
| ATCTTTGTACAGCTTTAAGTTGTGTCAGATTCTCTGAAAACATTTTTTAGA |
| AAGCAAAATTTTTATATTTGTTCAATTTCAGCTATACCCAAGTAGATTTAC |
| ATGTATATGAAGCAAATATTTTTAAAAATTTCTGTTTGTACATATTCTGCA |
| TGTTTTATAATTTCAAATGCATCACTTACATAGGTATTTCTCCCACAGAA |
| ATGATGAAAGTGACCAGAAAAAACAAAAACAAAACCCCTTTACTCTGTAGG |
| TCATTGAAACGAAGTAAGCTGGCAGCTGGTTTTATTGGAATGACAGTGTTC |
| TCGGAAGGAGCAGCCTACAAGATAACTTGAATTTGCCAATTCTGCAAAATC |
| TGTGCTTTTTTGAAAATTTAAGAGTGGGGACGTGAAACTGTATTCTGTGCC |
| TTCCATCATGATTTCCACATGAAAGCACTTTAAGGCACTGATTTTAAGATA |
| ATGTTTTTGGAAAACCCAATGCATATGGGTTTCTGAAATATTTTATGGACT |
| TATTTCTCCCCAGGAAATGATTCTTACGGAAAAAATTGCTTTTGTATGTA |
| GAACAGGAACTTTTTGTATTACAGTGATGCAATAGACATGTCTAATGTAAC |
| TTCTACTTTTCCTTTTGAAAGCTCAGTGTCTGTGCTATGACTTGCTCTCAT |
| CACAATATTGTTGAATTCCACAATGTATGGACATTAAACACTGGCAGACTG |
| TTCACTTTTTCTTTTTTTTTTGGTAAAATATTACTTCAAACCCCTTTTT |
| CTTGCTTTATTTTTCAGTGTTTTATTGCTTTATGAACTGTTTAACCCTGAA |
| ATCCCTCTAGGTTATCTATACTGTATAAAAAAGCAATTACCCTTAAAACTG |
| TACTCTGGCCTACTTTTCTATTTTGCAATTAAATATCTTTTTCACATATGT |
| TCATTGTAGACTTATGTTTTATCACATCTTATTAACACATTAAAAATGTT |
| ATCCTATGC | mRNA sequence of exon 9 of GABPB1L
(SEQ ID NO: 15)
GAGAGAGAAGCTCTTCAGAAACAGCTGGATGAAGCAAATCGAGAAGCACAA
AAATATCGACAGCAGCTCCTAAAGAAAGAACAGGAAGCAGAGGCCTACAGA
CAGAAGTTGGAAGCTATGACTCGTCTTCAGACTAATAAAGAAGCGTTTAA

What is claimed is:

1. A method for treating a brain cancer associated with a telomerase reverse transcriptase (TERT) promoter mutation in a subject comprising administering to the subject a therapeutically effective amount of an agent that specifically reduces or inhibits GA binding protein transcription factor beta subunit 1 long isoform (GABPB1L) expression or function, thereby treating a cancer associated with a TERT promoter mutation, wherein the agent is an antisense oligonucleotide comprising a sequence that specifically hybridizes to a nucleic acid sequence in the 3' untranslated region (UTR) of a GABPB1L mRNA.

2. The method of claim 1, further comprising identifying one or more mutations in the TERT promoter of the subject prior to administering the agent that specifically reduces or inhibits GABPB1L expression or function.

3. The method of claim 1, wherein the antisense oligonucleotide comprises a nucleotide sequence that is complementary to the sequence set forth as SEQ ID NO: 1, SEQ ID NO: 2 or SEQ ID NO: 3.

4. The method of claim 1, wherein the agent is an antisense oligonucleotide comprising a sequence that specifically hybridizes to a nucleic acid sequence of a GABPB1L mRNA, wherein the nucleotide sequence encodes exon 9 of GABPB1L.

5. The method of claim 4, wherein the antisense oligonucleotide comprises a nucleotide sequence that is complementary to the sequence set forth as SEQ ID NO: 4, SEQ ID NO: 5 or SEQ ID NO: 6.

6. The method of claim 1, wherein the antisense oligonucleotide is a locked nucleic acid (LNA) antisense oligonucleotide.

7. The method of claim 1, wherein the antisense oligonucleotide is between about 10 and about 50 nucleotides in length.

8. The method of claim 7, wherein the antisense oligonucleotide is between about 13 and about 25 nucleotides in length.

9. The method of claim 1, wherein the brain cancer is a glioblastoma, or an oligodendroglioma.

10. The method of claim 1, further comprising administering another cancer therapy to the subject.

11. The method of claim 10, wherein the cancer therapy is selected from the group consisting of radiation therapy, chemotherapy and surgery.

12. The method of claim 3, wherein the antisense oligonucleotide comprises SEQ ID NO: 7, SEQ ID NO: 8, or SEQ ID NO: 9.

* * * * *

SEQUENCE LISTING

<160> NUMBER OF SEQ ID NOS: 15

<210> SEQ ID NO 1
<211> LENGTH: 16
<212> TYPE: DNA
<213> ORGANISM: Artificial sequence
<220> FEATURE:
<223> OTHER INFORMATION: Synthetic construct

<400> SEQUENCE: 1
gatcgttgtt ggttag                                            16

<210> SEQ ID NO 2
<211> LENGTH: 16

```
<212> TYPE: DNA
<213> ORGANISM: Artificial sequence
<220> FEATURE:
<223> OTHER INFORMATION: Synthetic construct

<400> SEQUENCE: 2
actggcagac tgttca                                                    16

<210> SEQ ID NO 3
<211> LENGTH: 16
<212> TYPE: DNA
<213> ORGANISM: Artificial sequence
<220> FEATURE:
<223> OTHER INFORMATION: Synthetic construct

<400> SEQUENCE: 3
taattatggt ggactg                                                    16

<210> SEQ ID NO 4
<211> LENGTH: 16
<212> TYPE: DNA
<213> ORGANISM: Artificial sequence
<220> FEATURE:
<223> OTHER INFORMATION: Synthetic construct

<400> SEQUENCE: 4
tcgacagcag ctccta                                                    16

<210> SEQ ID NO 5
<211> LENGTH: 16
<212> TYPE: DNA
<213> ORGANISM: Artificial sequence
<220> FEATURE:
<223> OTHER INFORMATION: Synthetic construct

<400> SEQUENCE: 5
cctacagaca gaagtt                                                    16

<210> SEQ ID NO 6
<211> LENGTH: 16
<212> TYPE: DNA
<213> ORGANISM: Artificial sequence
<220> FEATURE:
<223> OTHER INFORMATION: Synthetic construct

<400> SEQUENCE: 6
taaagaagct gtttaa                                                    16

<210> SEQ ID NO 7
<211> LENGTH: 16
<212> TYPE: DNA
<213> ORGANISM: Artificial sequence
<220> FEATURE:
<223> OTHER INFORMATION: Synthetic construct

<400> SEQUENCE: 7
ctaaccaaca acgatc                                                    16

<210> SEQ ID NO 8
<211> LENGTH: 16
<212> TYPE: DNA
<213> ORGANISM: Artificial sequence
<220> FEATURE:
<223> OTHER INFORMATION: Synthetic construct

<400> SEQUENCE: 8
```

```
tgaacagtct gccagt                                                         16

<210> SEQ ID NO 9
<211> LENGTH: 16
<212> TYPE: DNA
<213> ORGANISM: Artificial sequence
<220> FEATURE:
<223> OTHER INFORMATION: Synthetic construct

<400> SEQUENCE: 9
cagtccacca taatta                                                         16

<210> SEQ ID NO 10
<211> LENGTH: 16
<212> TYPE: DNA
<213> ORGANISM: Artificial sequence
<220> FEATURE:
<223> OTHER INFORMATION: Synthetic construct

<400> SEQUENCE: 10
taggagctgc tgtcga                                                         16

<210> SEQ ID NO 11
<211> LENGTH: 16
<212> TYPE: DNA
<213> ORGANISM: Artificial sequence
<220> FEATURE:
<223> OTHER INFORMATION: Synthetic construct

<400> SEQUENCE: 11
aacttctgtc tgtagg                                                         16

<210> SEQ ID NO 12
<211> LENGTH: 16
<212> TYPE: DNA
<213> ORGANISM: Artificial sequence
<220> FEATURE:
<223> OTHER INFORMATION: Synthetic construct

<400> SEQUENCE: 12
ttaaacagct tcttta                                                         16

<210> SEQ ID NO 13
<211> LENGTH: 1604
<212> TYPE: DNA
<213> ORGANISM: Artificial sequence
<220> FEATURE:
<223> OTHER INFORMATION: Synthetic construct

<400> SEQUENCE: 13
cagaaataga agagagagaa gctcttcaga aacagctgga tgaagcaaat cgagaagcac         60
aaaaatatcg acagcagctc ctaaagaaag aacaggaagc agaggcctac agacagaagt        120
tggaagctat gactcgtctt cagactaata aagaagctgt ttaattgaaa tgaacatgta        180
gtttgatttt acttttggtc aagaaagaat acaatcttga actgtacaca acaaaggtac        240
agccatggga atacagaatg atagaagaga ctacagatgg ataattggac ttaagccatg        300
agctctgagt tcttgtaaca taaaacttta ctttagaagt tgtgaaatgt atttaaaact        360
gaattctgta aatagttttt tttttttac agttccaaat gagttgataa agattgttga        420
agagatccaa aaccagaata agccactgtt tttgtgaatt cttttttgatt ttagtacaaa       480 ccttaatttc tcagaaacgg aacagtttta agggtgatcg ttgttggtta ggccaaatgt       540
tgtgtaataa ttatggtgga ctgatgctgg aattactcct gtaggtataa acctctgtat       600
```

```
gaagagaaga tttctcccag gaaatctttg tacagcttta agttgtgtca gattctctga      660
aaacattttt tagaaagcaa aatttttata tttgttcaat ttcagctata cccaagtaga      720
tttacatgta tatgaagcaa atattttaa  aaatttctgt ttgtacatat tctgcatgtt      780
ttataatttc aaaatgcatc acttacatag gtatttctcc cacagaaatg atgaaagtga      840
ccagaaaaaa acaaaaacaa aaccccttta ctctgtaggt cattgaaacg aagtaagctg      900
gcagctggtt ttattggaat gacagtgttc tcggaaggag cagcctacaa gataacttga      960
atttgccaat tctgcaaaat ctgtgctttt ttgaaaattt aagagtgggg acgtgaaact     1020
gtattctgtg ccttccatca tgatttccac atgaaagcac tttaaggcac tgattttaag     1080
ataatgtttt tggaaaaccc aatgcatatg ggtttctgaa atattttatg gacttatttc     1140
tccccaggaa atgattctta cggaaaaaaa ttgcttttgt atgtagaaca ggaacttttt     1200
gtattacagt gatgcaatag acatgtctaa tgtaacttct acttttcctt ttgaaagctc     1260
agtgtctgtg ctatgacttg ctctcatcac aatattgttg aattccacaa tgtatggaca     1320
ttaaacactg gcagactgtt cacttttttct ttttttttt  tggtaaaata ttacttcaaa     1380
cccctttttc ttgctttatt tttcagtgtt ttattgcttt atgaactgtt taaccctgaa     1440
atccctctag gttatctata ctgtataaaa aagcaattac ccttaaaact gtactctggc     1500 ctactttttct attttgcaat taaatatctt tttcacatat gttcattgta gacttatgtt     1560
tttatcacat cttattaaca cattaaaaat gttatcctac tgca                      1604

<210> SEQ ID NO 14
<211> LENGTH: 1439
<212> TYPE: DNA
<213> ORGANISM: Artificial sequence
<220> FEATURE:
<223> OTHER INFORMATION: Synthetic construct

<400> SEQUENCE: 14
ttgaaatgaa catgtagttt gatttttactt ttggtcaaga aagaatacaa tcttgaactg      60
tacacaacaa aggtacagcc atgggaatac agaatgatag aagagactac agatggataa     120
ttggacttaa gccatgagct ctgagttctt gtaacataaa actttacttt agaagttgtg     180
aaatgtattt aaaactgaat tctgtaaata gttttttttt ttttacagtt ccaaatgagt     240
tgataaagat tgttgaagag atccaaaacc agaataagcc actgttttg  tgaattcttt     300 ttgattttag tacaaacctt aatttctcag aaacggaaca gttttaaggg tgatcgttgt     360
tggttaggcc aaatgttgtg taataattat ggtggactga tgctggaatt actcctgtag     420
gtataaacct ctgtatgaag agaagatttc tcccaggaaa tctttgtaca gctttaagtt     480
gtgtcagatt ctctgaaaac attttttaga agcaaaatt  tttatatttg ttcaatttca     540 gctatacccca gtagattta  catgtatatg aagcaaatat ttttaaaaat ttctgtttgt     600
acatattctg catgttttat aatttcaaaa tgcatcactt acataggtat ttctcccaca     660
gaaatgatga aagtgaccag aaaaaaacaa aaacaaaacc cctttactct gtaggtcatt     720
gaaacgaagt aagctggcag ctggttttat tggaatgaca gtgttctcgg aaggagcagc     780
ctacaagata acttgaattt gccaattctg caaaatctgt gctttttga  aaatttaaga     840 gtggggacgt gaaactgtat tctgtgcctt ccatcatgat ttccacatga aagcacttta     900
aggcactgat tttaagataa tgttttttgga aaacccaatg catatgggtt tctgaaatat     960
tttatggact tatttctccc caggaaatga ttcttacgga aaaaaattgc ttttgtatgt    1020
```

```
agaacaggaa cttttgtat tacagtgatg caatagacat gtctaatgta acttctactt    1080
ttccttttga aagctcagtg tctgtgctat gacttgctct catcacaata ttgttgaatt    1140
ccacaatgta tggacattaa acactggcag actgttcact ttttctttt ttttttggt     1200 aaaatattac ttcaaacccc tttttcttgc tttattttc agtgttttat tgctttatga    1260
actgtttaac cctgaaatcc ctctaggtta tctatactgt ataaaaagc aattaccctt    1320 aaaactgtac tctggcctac ttttctattt tgcaattaaa tatcttttc acatatgttc    1380 attgtagact tatgttttta tcacatctta ttaacacatt aaaaatgtta tcctactgc    1439
```

<210> SEQ ID NO 15
<211> LENGTH: 153
<212> TYPE: DNA
<213> ORGANISM: Artificial sequence
<220> FEATURE:
<223> OTHER INFORMATION: Synthetic construct

<400> SEQUENCE: 15

```
gagagagaag ctcttcagaa acagctggat gaagcaaatc gagaagcaca aaaatatcga      60
cagcagctcc taaagaaaga acaggaagca gaggcctaca gacagaagtt ggaagctatg     120
actcgtcttc agactaataa agaagctgtt taa                                  153
```